US010691970B2

(12) United States Patent
Ito

(10) Patent No.: US 10,691,970 B2
(45) Date of Patent: *Jun. 23, 2020

(54) DATA ACQUIRING APPARATUS, PRINTING APPARATUS, AND GENUINENESS DISCRIMINATING APPARATUS

(71) Applicant: FUJI XEROX CO., LTD., Tokyo (JP)

(72) Inventor: Kensuke Ito, Yokohama (JP)

(73) Assignee: FUJI XEROX CO., LTD., Tokyo (JP)

( * ) Notice: Subject to any disclaimer, the term of this patent is extended or adjusted under 35 U.S.C. 154(b) by 147 days.

This patent is subject to a terminal disclaimer.

(21) Appl. No.: 15/765,674

(22) PCT Filed: Apr. 22, 2016

(86) PCT No.: PCT/JP2016/062741
§ 371 (c)(1),
(2) Date: Apr. 3, 2018

(87) PCT Pub. No.: WO2017/085952
PCT Pub. Date: May 26, 2017

(65) Prior Publication Data
US 2019/0087678 A1 Mar. 21, 2019

(30) Foreign Application Priority Data

Nov. 18, 2015 (JP) ................. 2015-225265

(51) Int. Cl.
*G06K 9/00* (2006.01)
*G06K 9/42* (2006.01)
(Continued)

(52) U.S. Cl.
CPC ............... *G06K 9/42* (2013.01); *A61J 3/007* (2013.01); *A61J 3/06* (2013.01); *B41F 17/36* (2013.01);
(Continued)

(58) Field of Classification Search
CPC .. A61J 3/007; A61J 3/06; B41F 17/36; G01N 21/85; G06K 9/42; G06K 9/623; G07D 5/02; G16H 20/13
See application file for complete search history.

(56) References Cited

U.S. PATENT DOCUMENTS 8,712,163 B1  4/2014 Osheroff
9,033,447 B2  5/2015 Morita et al.
(Continued)

FOREIGN PATENT DOCUMENTS

CN  103492862 A  1/2014
CN  103781714 A  5/2014
(Continued)

OTHER PUBLICATIONS

Jul. 5, 2016 International Search Report issued in International Patent Application No. PCT/JP2016/062741.
(Continued)

*Primary Examiner* — Nirav G Patel
(74) *Attorney, Agent, or Firm* — Oliff PLC

(57) ABSTRACT

A data acquiring apparatus includes: an acquirer that acquires feature data, as registration data, from an image including an object to be registered, the feature data representing a feature that is distributed in a region of a predetermined size determined based on a position defined by an external shape of the object and a position of printing information that has been printed on the object; and a memory that stores the registration data acquired by the acquirer as data for determining identity of the object.

9 Claims, 29 Drawing Sheets

(51) Int. Cl.
*A61J 3/06* (2006.01)
*G16H 20/13* (2018.01)
*G01N 21/85* (2006.01)
*G07D 5/02* (2006.01)
*A61J 3/00* (2006.01)
*B41F 17/36* (2006.01)
*G06K 9/62* (2006.01)

(52) U.S. Cl.
CPC ............ *G01N 21/85* (2013.01); *G06K 9/623* (2013.01); *G07D 5/02* (2013.01); *G16H 20/13* (2018.01)

(56) References Cited

U.S. PATENT DOCUMENTS

| | | | |
|---|---|---|---|
| 2006/0180515 A1* | 8/2006 | Kimura | G07D 7/2033 209/547 |
| 2013/0188038 A1 | 7/2013 | Tanimoto et al. | |
| 2014/0079326 A1 | 3/2014 | Ito et al. | |
| 2014/0148943 A1 | 5/2014 | Matsunoshita | |
| 2014/0226020 A1 | 8/2014 | Ito | |
| 2015/0010758 A1 | 1/2015 | Ito et al. | |
| 2015/0170373 A1 | 6/2015 | Yonaha et al. | |
| 2018/0350058 A1 | 12/2018 | Ito et al. | |

FOREIGN PATENT DOCUMENTS

| | | |
|---|---|---|
| CN | 104125820 A | 10/2014 |
| CN | 104717952 A | 6/2015 |
| EP | 2 829 260 A1 | 1/2015 |
| JP | H03-274153 A | 12/1991 |
| JP | 4103826 B2 | 6/2008 |
| JP | 2009-290674 A | 12/2009 |
| JP | 2013-025557 A | 2/2013 |
| JP | 2013-121432 A | 6/2013 |
| JP | 2015-016303 A | 1/2015 |
| WO | 2010/072745 A1 | 7/2010 |
| WO | 2013/140639 A1 | 9/2013 |

OTHER PUBLICATIONS

Jul. 5, 2016 Written Opinion of the International Searching Authority issued in International Patent Application No. PCT/JP2016/062741.
Jun. 5, 2019 Partial Supplementary Search Report issued in European Patent Application No. 16865955.5.
Dec. 25, 2019 Office Action issued in Japanese Patent Application No. 2015-225265.
Oct. 9, 2019 Office Action issued in Chinese Patent Application No. 201680065125.X.
Apr. 1, 2020 Office Action issued in Japanese Patent Application No. 2015-225265.

* cited by examiner

81
REGISTRATION DATA
ACQUISITION REGION

REGISTRATION DATA

32 X 32 DOTS

COLLATION DATA

64 X 64 DOTS

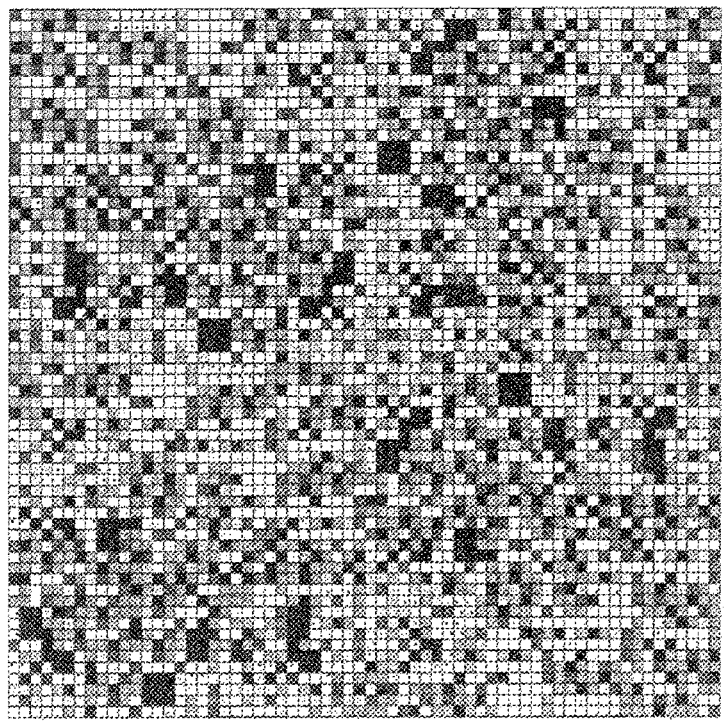
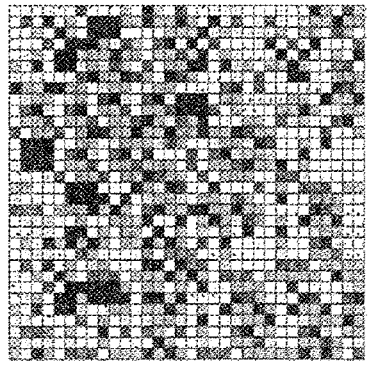
FIG. 14

FIG. 15
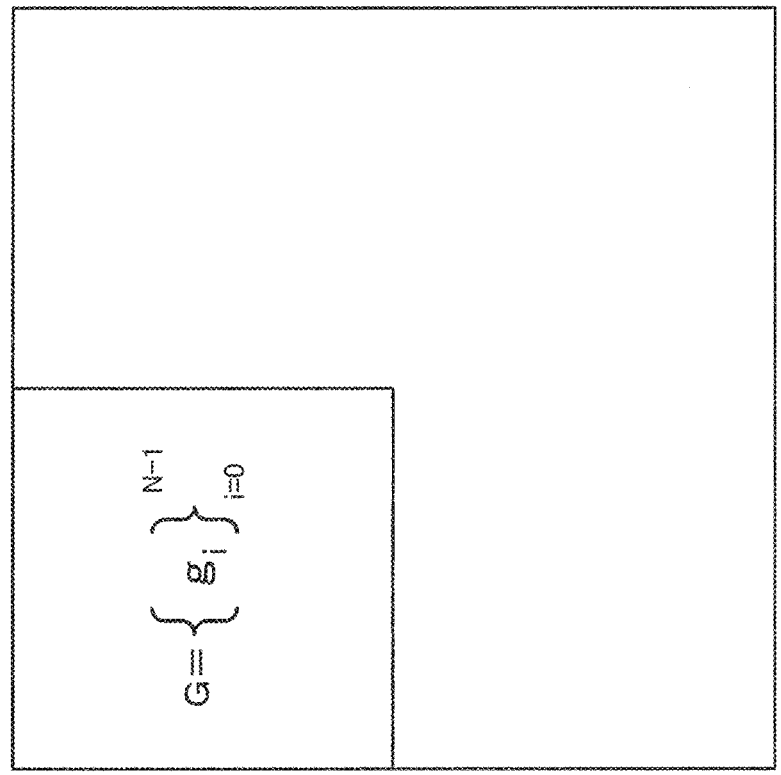
COLLATION DATA
64 X 64 DOTS
$G = \{g_i\}_{i=0}^{N-1}$
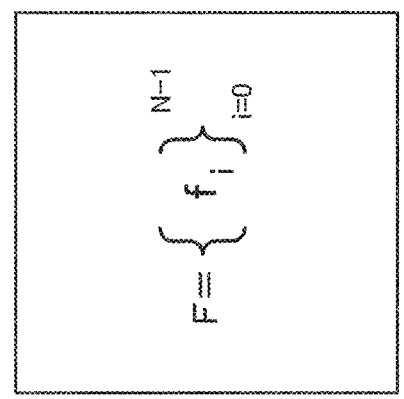
REGISTRATION DATA
32 X 32 DOTS
$F = \{f_i\}_{i=0}^{N-1}$

FIG. 26
(A)
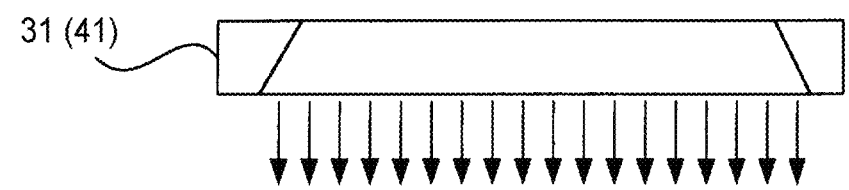
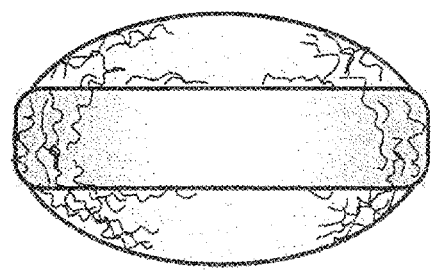
(B)
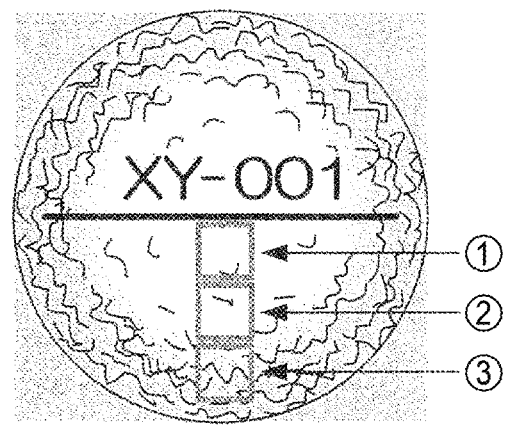
③＞②＞①

FIG. 28
(A)
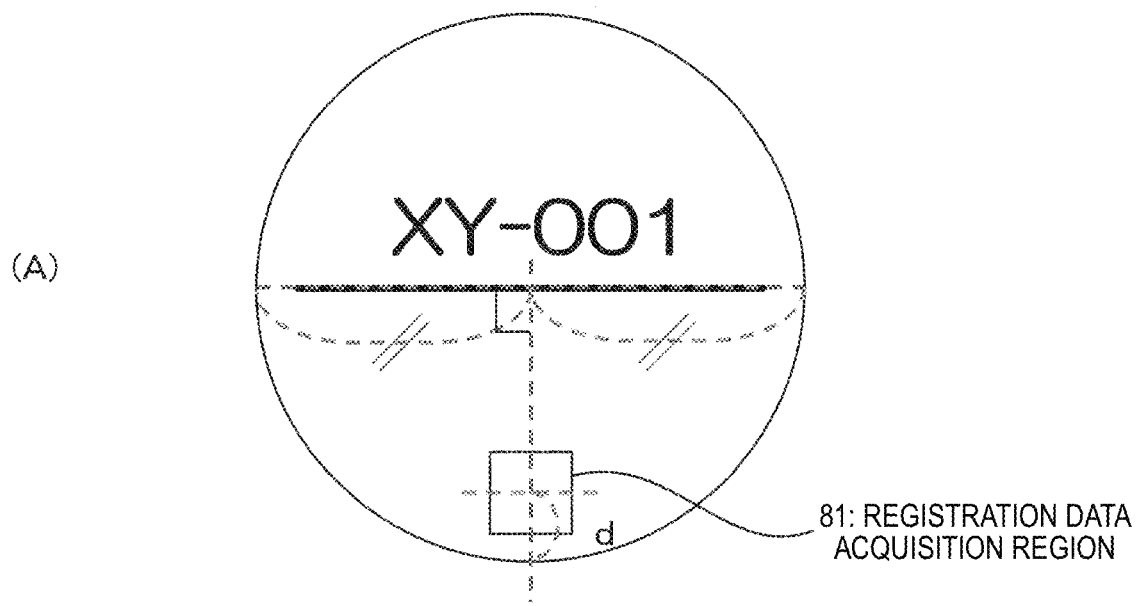
81: REGISTRATION DATA ACQUISITION REGION
(B)
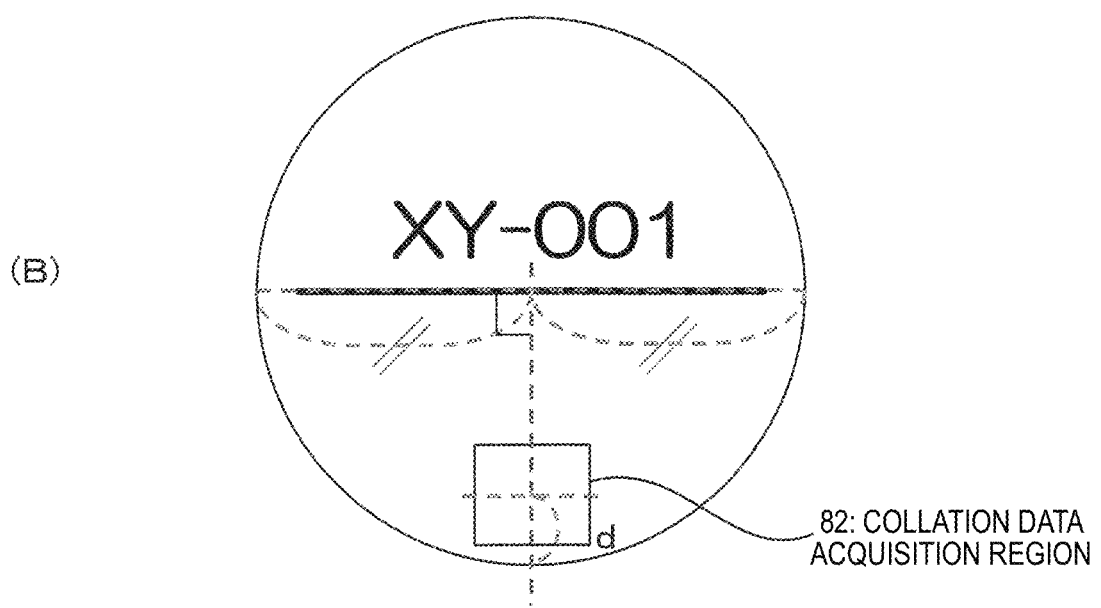
82: COLLATION DATA ACQUISITION REGION

DATA ACQUIRING APPARATUS, PRINTING APPARATUS, AND GENUINENESS DISCRIMINATING APPARATUS

CROSS-REFERENCE TO RELATED APPLICATIONS

This application is based on and claims priority under 35 USC 119 from Japanese Patent Application No. 2015-225265 filed on Nov. 18, 2015.

BACKGROUND

Technical Field

The present invention relates to a data acquiring apparatus, a printing apparatus, a genuineness discriminating apparatus, a method and a program.

SUMMARY

According to an aspect of the invention, there is provided a data acquiring apparatus comprising: an acquirer that acquires feature data, as registration data, from an image including an object to be registered, the feature data representing a feature that is distributed in a region of a predetermined size determined based on a position defined by an external shape of the object and a position of printing information that has been printed on the object; and a memory that stores the registration data acquired by the acquirer as data for determining identity of the object.

BRIEF DESCRIPTION OF DRAWINGS

Exemplary embodiments of the present invention will be described in detail based on the following figures, wherein:

FIG. 14 is a view showing the example of the registration data and the example of the collation data which are targets of collation calculation;

FIG. 15 is a view for explaining a state in which data having same size as the registration data is sequentially cut out of the collation data;

FIG. 26 is a view for explaining a state of a case where light emitted from a ring illumination unit 31 (41) is radiated onto a circular tablet, in which (A) of FIG. 26 is a view of the tablet seen from a side surface side, and (B) of FIG. 26 is a view of the tablet seen from an upper surface side;

FIG. 28 is a view for explaining a procedure when positions of data acquisition regions are determined, in which (A) of FIG. 28 is a view for explaining a procedure when a registration data acquirer 22 determines a position of a registration data acquisition region 81, and (B) of FIG. 28 is a view for explaining the procedure when a collation data acquirer 25 determines a position of a collation data acquisition region 82;

DETAILED DESCRIPTION

Next, exemplary embodiments of the invention will be described in detail with reference to the drawings.

First Exemplary Embodiment

Figure 1:
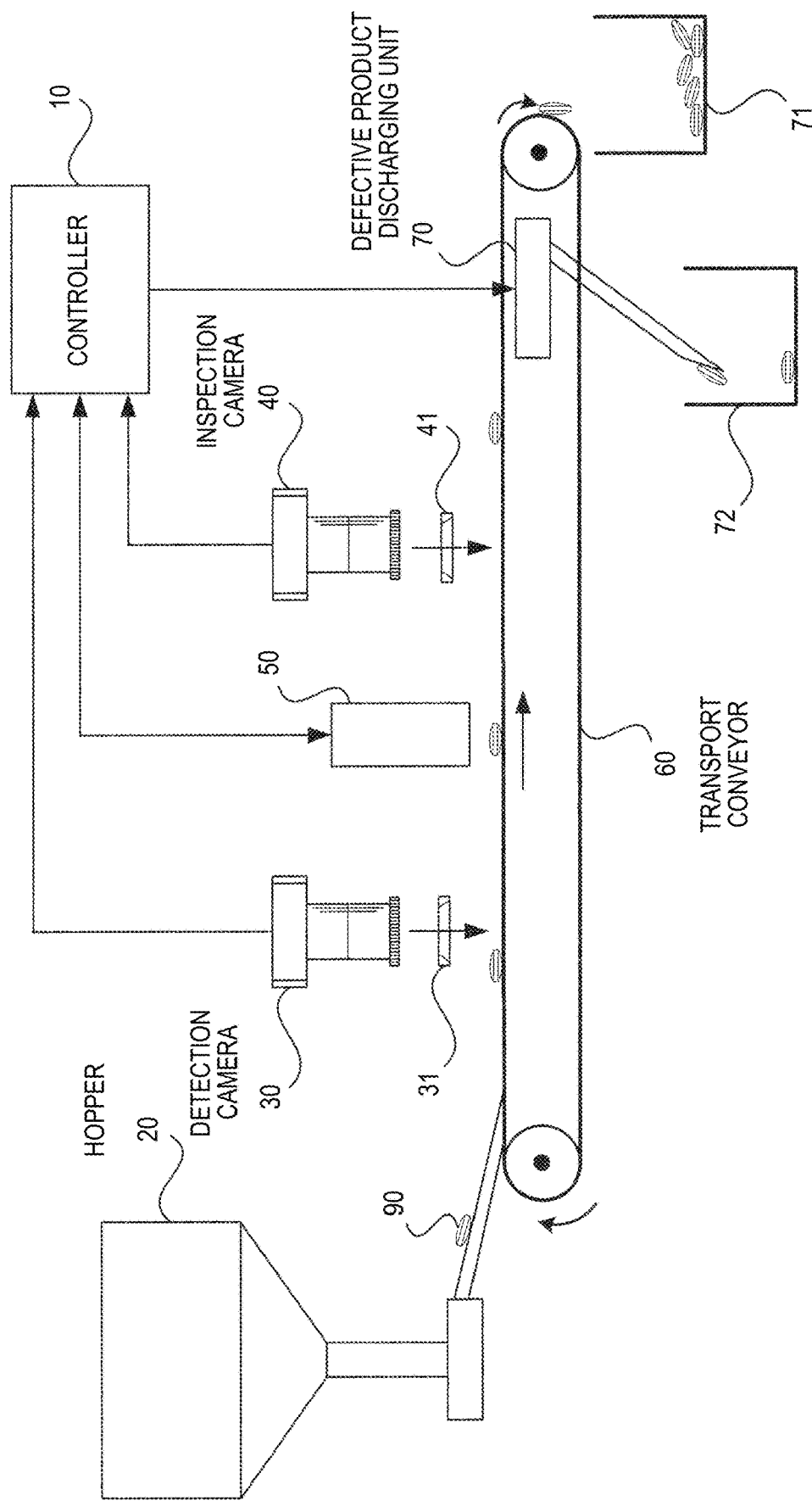
FIG. 1 is a view showing a configuration of a printing apparatus according to a first exemplary embodiment of the invention.

First, a printing apparatus according to a first exemplary embodiment of the invention will be described. FIG. 1 is a view showing a configuration of the printing apparatus according to the first exemplary embodiment of the invention.

In the printing apparatus for printing printing information of characters etc. on a circular tablet according to the exemplary embodiment, feature data based on which the tablet can be identified uniquely is acquired and stored as registration data (registration image data) when printing is performed on the tablet.

Incidentally, since registration data of all tablets on which printing processing has been performed are acquired and stored in advance in this manner, the tablets can be discriminated from one another. For example, assume that a tablet which is suspected to be counterfeit has been found in the market. In this case, feature data of the tablet collected from the market and suspected to be counterfeit is acquired and compared with all the stored registration data. Thus, determination can be made as to whether the tablet is a genuinely manufactured and shipped tablet or a counterfeit tablet.

Incidentally, a case where printing is performed on the circular tablet will be described in the exemplary embodiment. However, the invention may be also applied to a tablet having another shape than the circular shape in a similar manner. In addition, the invention may be also applied to any kind of tablet, a coated tablet such as a film-coated tablet or a sugar-coated tablet, or an uncoated tablet (naked tablet).

Further, the circular tablet is used as an example of an object in the invention. However, the invention may be applied to any object as long as the object has a readable unique feature with randomness, such as fine surface unevenness, distributed along the front surface. For example, the invention may be also applied to items using various objects including a chip component such as a chip capacitor, a component such as a gear or a washer, an IC chip, a semiconductor component, a credit card, a ticket, securities and a document.

As shown in FIG. 1, the printing apparatus according to the exemplary embodiment includes a controller 10, a hopper 20 for feeding tablets 90, a detection camera 30, a ring illumination unit 31, an inspection camera 40, a ring illumination unit 41, a print head portion 50, a transport conveyor (transport path) 60 for transporting the tablets 90 fed by the hopper 20, a defective product discharging unit 70, a good product storing box 71, and a defective product storing box 72.

Each of the ring illumination units 31 and 41 is an illumination device for radiating light onto the tablets 90 which are transported on the transport conveyor 60.

The detection camera 30 is an imager which captures an image (first image) including each of the tablets transported on the transport conveyor 60. The detection camera 30 is provided directly above the ring illumination unit 31. The detection camera 30 can capture an image of the tablet 90 onto which light is radiated by the ring illumination unit 31. Since the image of the tablet 90 is captured by the detection camera 30, a position, a direction, or the like of the tablet can be detected.

The print head portion 50 is a printer which performs printing on the tablet 90 based on the image captured by the detection camera 30. Here, the print head portion 50 uses an inkjet method to print characters, numerals, symbols, etc. of a manufacturing number, a lot number, a trade name etc. on the tablet 90 which is transported on the transport conveyor 60.

Specifically, printing operation of the print head portion 50 is controlled by the controller 10. The controller 10 detects information about the position or direction of the tablet 90 and the front/back etc. thereof based on the image captured by the detection camera 30. The controller 10 controls the print head portion 50 at a timing when designated characters etc. are printed at a designated position on the tablet 90 on the transport conveyor 60 based on the detected information.

Incidentally, since the tablet 90 is a circular tablet without any cleavage line, information about the direction or the front/back of the tablet 90 does not have to be detected in the exemplary embodiment. When printing is performed on a circular tablet with a cleavage line, the direction of the tablet on the transport conveyor 60 or the front/back based on presence/absence of the cleavage line is determined, and a printing controller 21 controls a direction etc. of the characters to be printed based on a result of the determination.

The inspection camera 40 is an imager which captures an image (second image) including the tablet 90 on which printing has been performed by the print head portion 50. The inspection camera 40 is provided directly above the ring illumination unit 41, and can capture an image of the tablet 90 onto which light is radiated by the ring illumination unit 41. The inspection camera 40 is provided in order to detect and exclude any tablet 90 having printing failure such as printing misalignment or printing blur.

The defective product storing box 72 is a discharge place for storing defective tablets discharged by the defective product discharging unit 70. The good product storing box 71 is a storage place for storing good tablets not discharged by the defective product discharging unit 70.

The defective product discharging unit 70 performs an operation of discharging any tablet 90 transported on the transport conveyor 60 into the defective product storing box 72 based on the control of the controller 10.

Based on the image captured by the inspection camera 40, the controller 10 checks a printing state of the tablet 90 in the image. When the printing state is determined as printing failure, the controller 10 controls the defective product discharging unit 70 which thereby discharges the defective tablet 90 into the defective product storing box 72.

Figure 2:
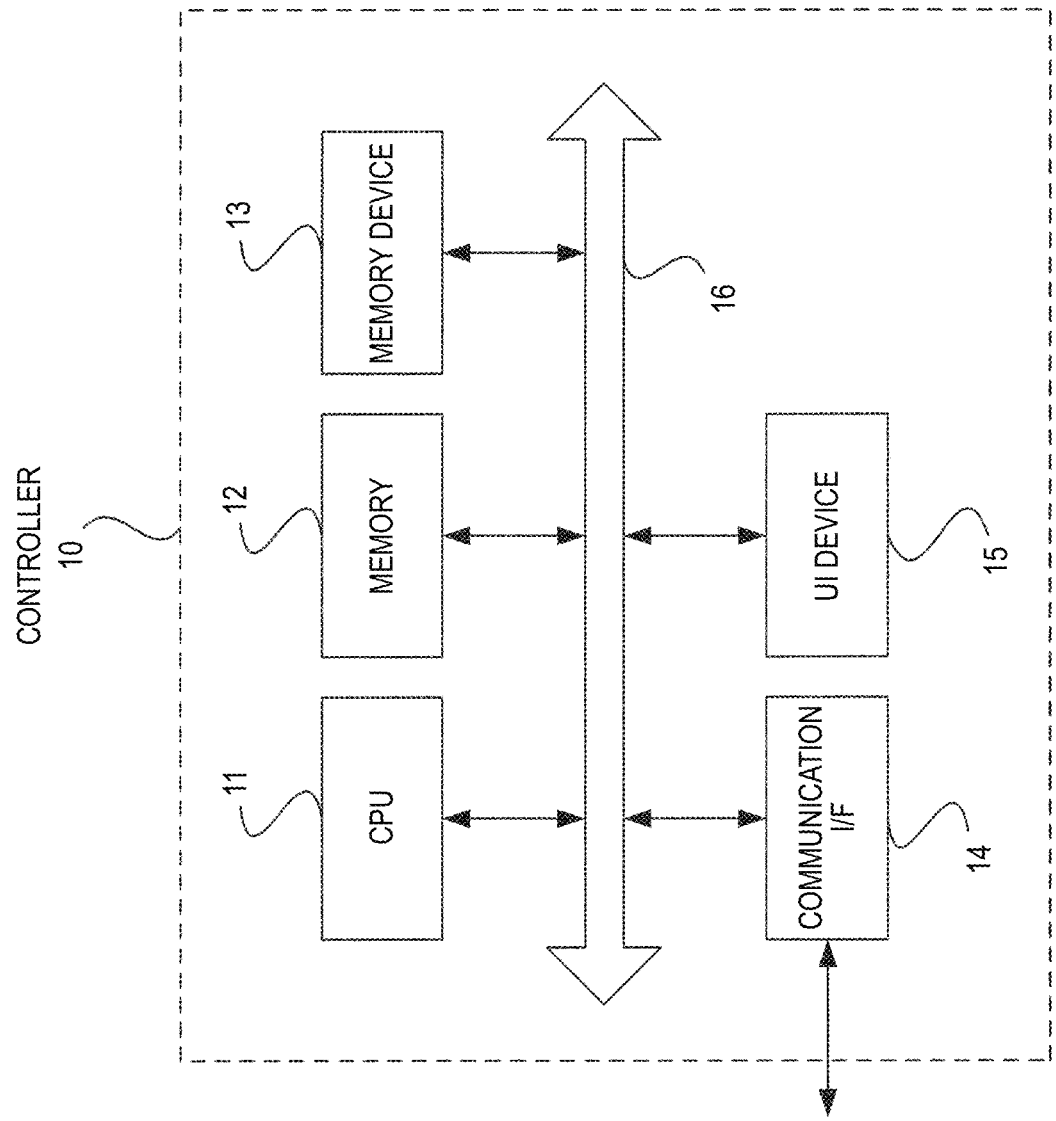
FIG. 2 is a block diagram showing a hardware configuration of a controller 10 in the first exemplary embodiment of the invention.

FIG. 2 shows hardware a configuration of the controller 10 in the printing apparatus according to the exemplary embodiment.

As shown in FIG. 2, the controller 10 has a CPU 11, a memory 12, a memory device 13 such as a hard disk drive (HDD), a communication interface (IF) 14 performing transmission and reception of data to and from internal devices such as the detection camera 30, the print head portion 50, the inspection camera 40 and the defective product discharging unit 70, and a user interface (UI) device 15 including a touch panel or a liquid crystal display and a keyboard. These constituent elements are connected to one another through a control bus 16.

The CPU 11 executes predetermined processing based on a control program stored in the memory 12 or the memory device 13, so as to control operation of the controller 10. Incidentally, in the exemplary embodiment, the CPU 11 is described as a device which reads and executes the control program stored in the memory 12 or the memory device 13. However, the program may be stored in a memory medium such as a CD-ROM and provided to the CPU 11.

Figure 3:
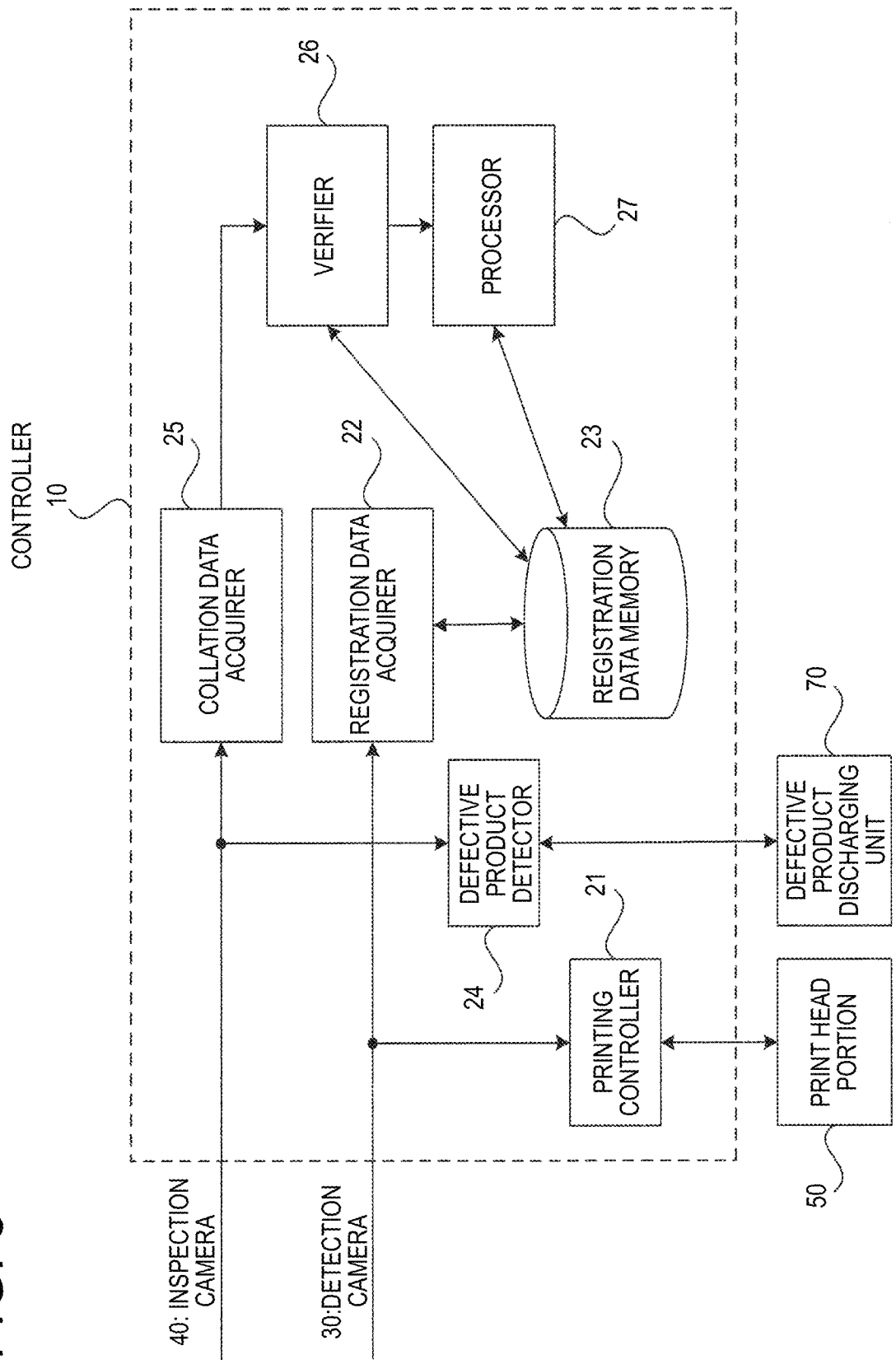
FIG. 3 is a block diagram showing a functional configuration of the controller 10 in the first exemplary embodiment of the invention.

FIG. 3 is a block diagram showing a functional configuration of the controller 10 achieved by execution of the aforementioned control program.

As shown in FIG. 3, the controller 10 according to the exemplary embodiment includes the printing controller 21, a registration data acquirer 22, a registration data memory 23, a defective product detector 24, a collation data acquirer 25, a verifier 26, and a processor 27.

The printing controller 21 detects a position of the tablet 90 to be printed, from the image captured by the detection camera 30, and controls a printing timing of the print head portion 50 based on the detected position. That is, the printing controller 21 calculates a timing for outputting a printing instruction to the print head portion 50, from information about transport speed of the transport conveyor 60, the position of the tablet 90 in the captured image, printing speed of the print head portion 50, etc., and transmits the printing instruction to the print head portion 50 at the calculated timing.

The defective product detector 24 determines whether or not there is a problem such as printing blur or printing misalignment in printing information of the characters etc. printed on the tablet 90, from the image including the tablet 90 which is imaged after the printing by the inspection camera 40. When there is printing failure, the detective product detector 24 controls the defective product discharging unit 70 which thereby discharges the tablet 90 from the transport conveyor 60. Incidentally, the defective product detector 24 detects not only the printing failure but also a problem such as chipping of the tablet 90.

The registration data acquirer 22 acquires feature data, as registration data, from the image captured by the detection camera 30, the feature data representing a feature distributed in a first region of a predetermined size on the front surface of the tablet 90. Specifically, the registration data acquirer 22 acquires a 32×32 dot region in a preset registration data acquisition region of the tablet 90, as the registration data.

Figure 4:
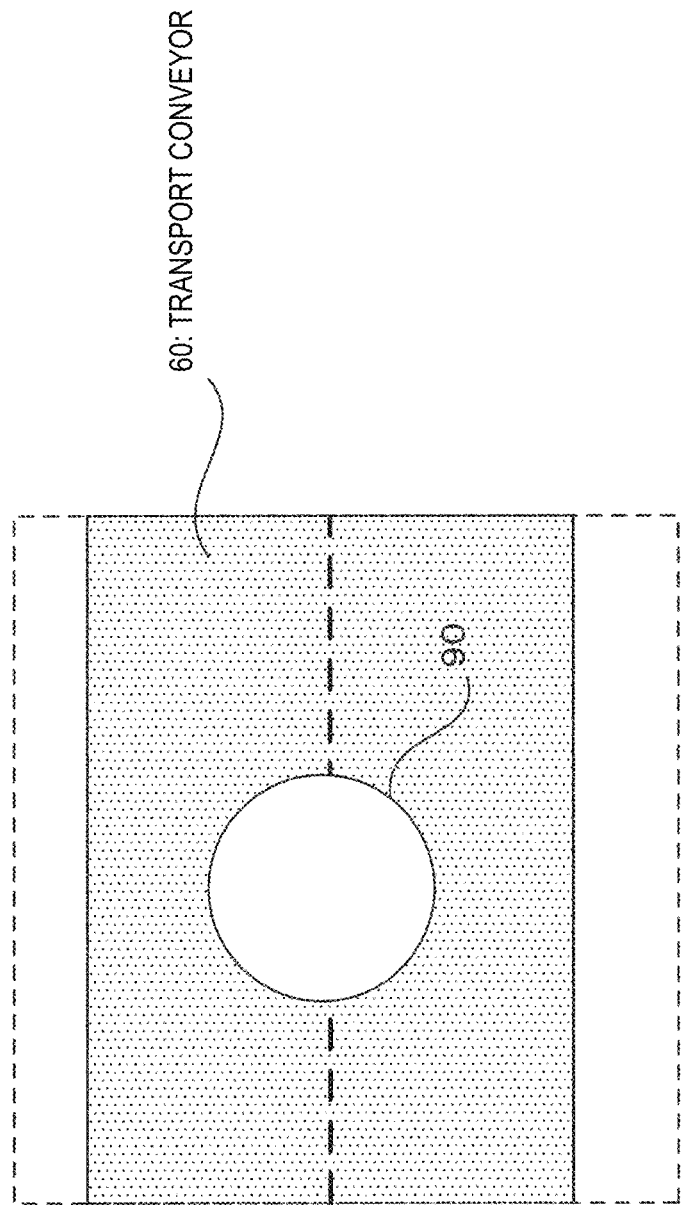
FIG. 4 is a view schematically showing an image captured by a detection camera 30.

FIG. 4 shows a schematic view of, for example, an image captured by the detection camera 30. In addition, FIG. 5 shows an example of an actually captured tablet image and an example of a position of a registration data acquisition region 81.

In FIG. 4, a state in which the image including a tablet 90 on the transport conveyor 60 is captured is shown.

Figure 5:
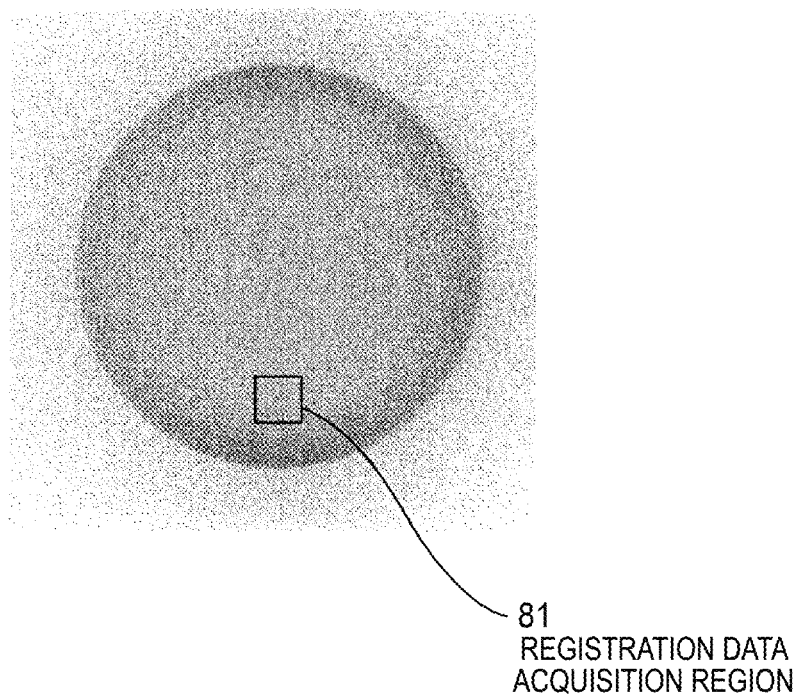
FIG. 5 is a view showing an example of an actually acquired tablet image and an example of a position of a registration data acquisition region 81.

In addition, in FIG. 5, it can be known that the registration data acquisition region 81 is set at a predetermined position on the actually captured tablet image. The registration data acquisition region 81 is determined based on an external shape of the tablet and a position defined by a position of a printing pattern (printing information) scheduled to be printed on the tablet. Incidentally, in the exemplary embodiment, details of the reason why the position of the region for acquiring registration data is determined based on both the external shape and the printing pattern of the tablet will be described later.

Figure 6:
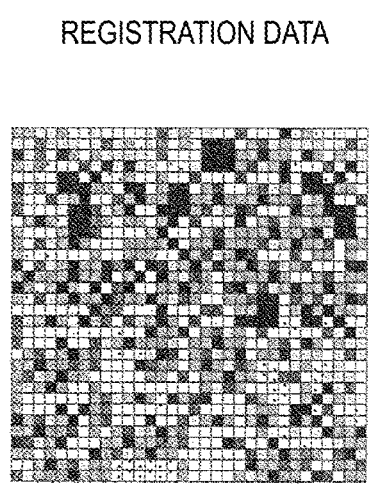
FIG. 6 is a view showing an example of registration data.

FIG. 6 shows an example of registration data obtained by cutting out data of a 32×32 dot region in the registration data acquisition region 81.

In the example of the registration data shown in FIG. 6, it can be known that concentration values of respective pixels of 1,024 (32×32) dots are acquired as data.

The printing controller 21 controls the print head portion 50 to execute processing of printing the designated characters etc. on the tablet 90 based on the position of the tablet 90 in the image captured by the detection camera 30.

Figure 7:
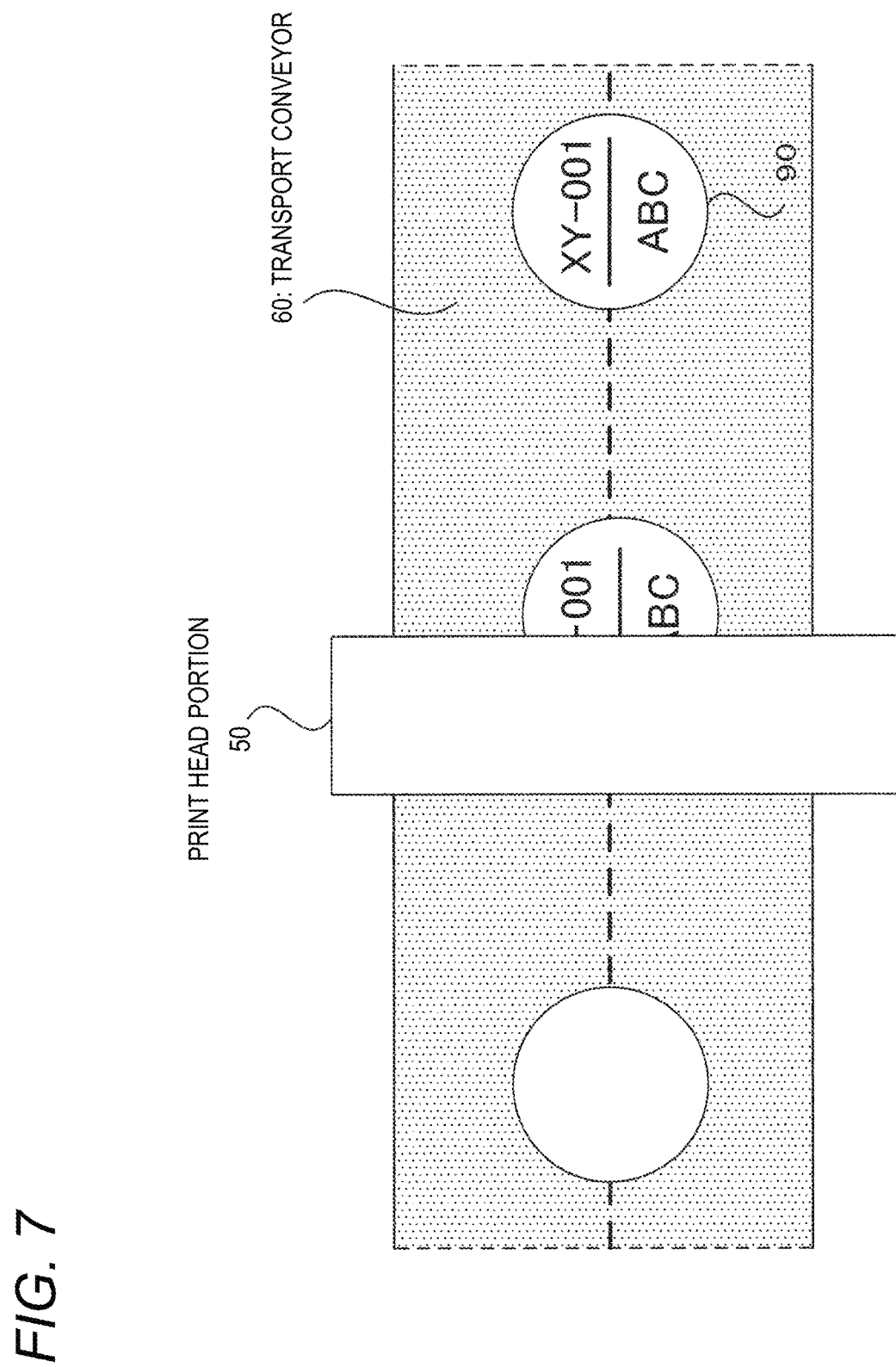
FIG. 7 is a view showing a state in which printing processing is performed by a print head portion 50.

FIG. 7 shows a state in which printing processing is performed thus by the print head portion 50. Refer to FIG. 7. It can be known that characters "XY-001" and "ABC" and a horizontal line (line) are printed on tablets 90 when each of the tablets 90 is passed under the print head portion 50 by the transport conveyor 60.

The collation data acquirer 25 acquires feature data as collation data (collation image data) from an image captured by the inspection camera 40, the feature data representing a feature distributed in a second region of a predetermined size on the tablet 90. The collation data acquirer 25 acquires the feature data as the collation data, the feature data representing the feature distributed in a collation data acquisition region (the second region) which includes the registration data acquisition region (first region) 81 on the tablet and which is larger in size than the registration data acquisition region 81.

Specifically, the collation data acquirer 25 acquires a 64×64 dot image in the preset collation data acquisition region of the tablet 90, as the collation data.

Incidentally, the position of the region for acquiring registration data is defined based on the printing pattern and the external shape, as described above. Therefore, the position of the region for acquiring collation data is also defined based on both the printing pattern and the external shape.

Figure 8:
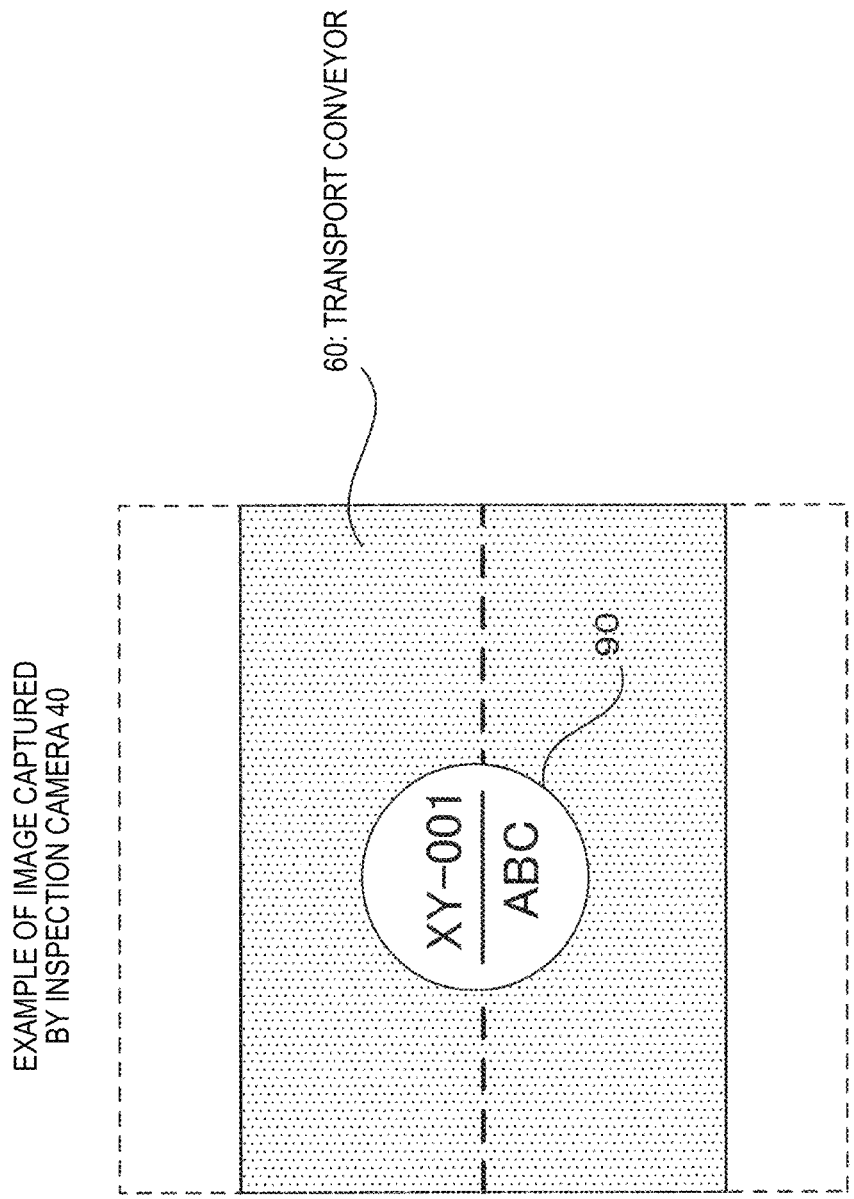
FIG. 8 is a view schematically showing an image captured by an inspection camera 40.

FIG. 8 shows a schematic view of, for example, an image captured by the inspection camera 40. In addition, FIG. 9 shows an example of an actually captured tablet image and an example of a position of a collation data acquisition region 82.

In FIG. 8, a state in which the image including the tablet 90 which is transported on the transport conveyor 60 after the printing is captured is shown.

Figure 9:
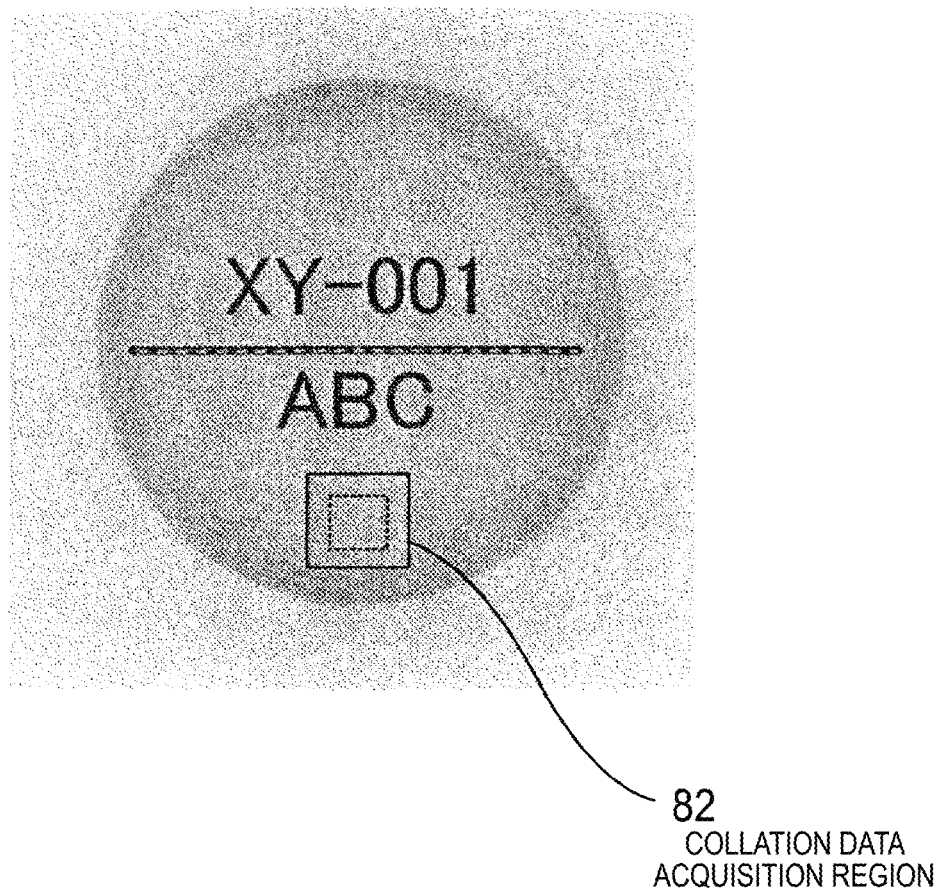
FIG. 9 is a view showing an example of an actually acquired tablet image and an example of a position of a collation data acquisition region 82.

In addition, in FIG. 9, it can be known that the collation data acquisition region 82 is set at a predetermined position on the actually acquired tablet image. The collation data acquisition region 82 is a wider region including the registration data acquisition region 81.

In the exemplary embodiment, each of the positions of the registration data acquisition region 81 and the collation data acquisition region 82 is defined based on both the position of the printing pattern of the printed characters etc. and the external shape. Specifically, each of the registration data acquisition region 81 and the collation data acquisition region 82 is defined based on a position determined from the horizontal line (line) printed on the tablet and the external shape.

Figure 10:
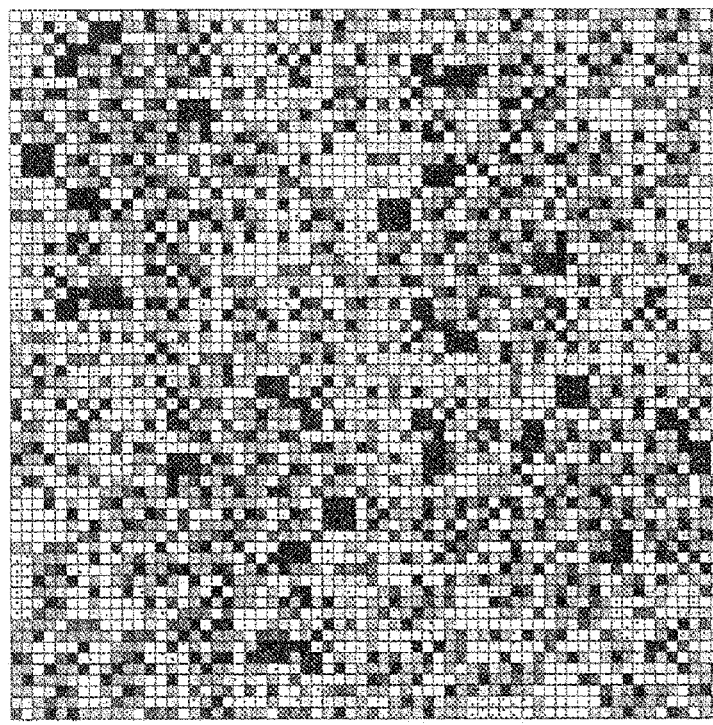
FIG. 10 is a view showing an example of collation data.

FIG. 10 shows an example of collation data obtained by cutting out data of a 64×64 dot region in the collation data acquisition region 82.

In the example of the registration data shown in FIG. 10, it can be known that concentration values of respective pixels of 4,096 (64×64) dots are acquired as data.

Figure 11:
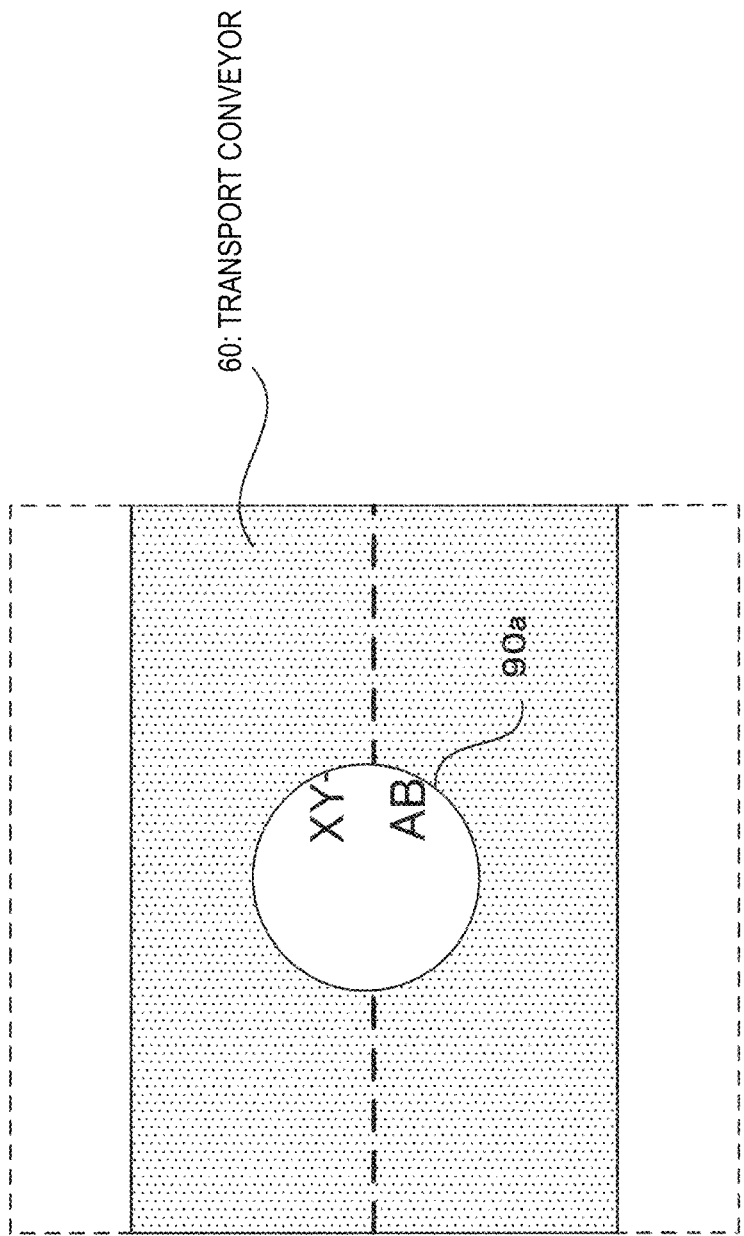
FIG. 11 is a view showing an example of an image captured by the inspection camera 40 in a case where printing was not performed on the tablet properly.

FIG. 11 shows an example of an image captured by the inspection camera 40 in a case where printing was not performed properly on a tablet by printing processing by the print head portion 50. A state in which a tablet 90a having printing failure is imaged is shown in the example of the image shown in FIG. 11.

When the image shown in FIG. 11 is captured by the inspection camera 40, the defective product detector 24 controls the defective product discharging unit 70 which thereby discharges the defective tablet 90a into the defective product storing box 72.

The registration data memory 23 stores the registration data acquired by the registration data acquirer 22, as data for determining identity of the tablet. Incidentally, when there is an empty space in storage capacity of the registration data memory 23, the entire image of the tablet after the printing may be stored as the registration data.

The verifier 26 compares the registration data stored in the registration data memory 23 with collation data in the same tablet acquired by the collation data acquirer 25, and verifies whether reliability of the registration data is equal to or larger than a predetermined criterion value or not.

For example, the verifier 26 calculates a correlation value between the registration data and data acquired from a corresponding region of the collation data. When the calculated correlation value satisfies a predetermined criterion, the verifier 26 outputs a verification result that the reliability of the registration data is equal to or larger than the predetermined criterion value.

Specifically, the verifier 26 sequentially selects data having same size as the registration data from the collation data, and sequentially calculates a correlation value between the selected data and the registration data by a normalized correlation method to consequently acquire plural correlation values. When a maximum of the acquired correlation values is equal to or larger than a first predetermined value, and a normalized score of the maximum of the correlation values is equal to or larger than a second predetermined value, the verifier 26 outputs a verification result that the reliability of the registration data is equal to or larger than the predetermined criterion value. The normalized score of the maximum of the correlation values is obtained by subtracting an average of the correlation values from the maximum of the correlation values and dividing a value obtained thus by a standard deviation of the correlation values.

Incidentally, a specific calculation method of each of the correlation values or a specific calculation method of the normalized score will be described later.

The processor 27 executes processing based on the verification result in the verifier 26. For example, the processor 27 issues an instruction to the registration data memory 23 to store information of the verification result in the verifier 26. Thus, the registration data memory 23 stores the information of the verification result in the verifier 26 corresponding to the registration data together with the registration data.

Figure 12:
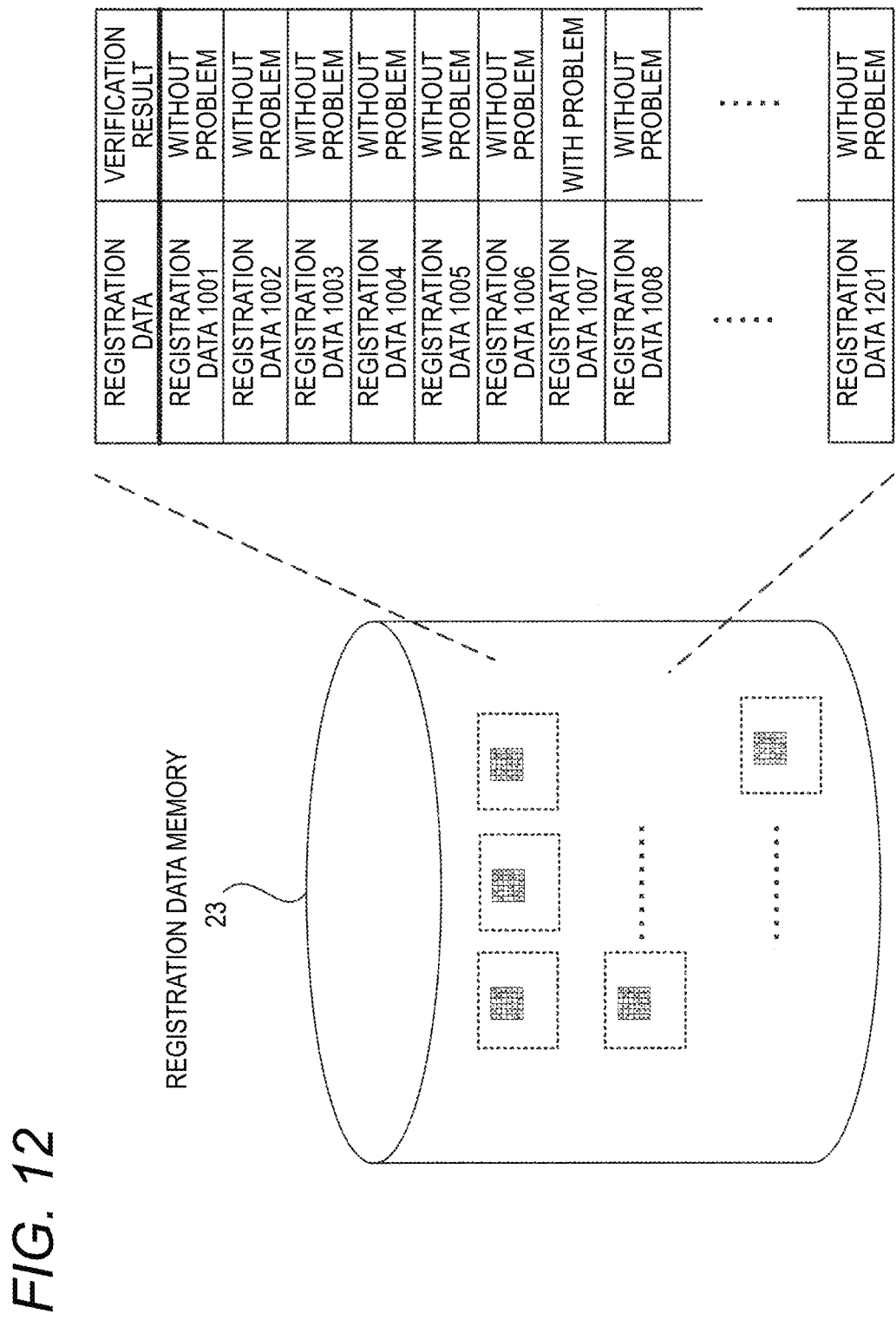
FIG. 12 is a view showing an example of data stored in a registration data memory 23.

FIG. 12 shows an example of data stored in the registration data memory 23. In the example shown in FIG. 12, it can be known that verification results of stored registration data are stored together with the registration data. For example, in the example shown in FIG. 12, "registration data 1007" indicates that reliability does not satisfy the predetermined criterion value in a verification result by the verifier 26, and there is a possibility that the tablet which is genuine may be wrongly determined as a counterfeit tablet when collation processing is performed thereon in the future.

In addition, the processor 27 may make control to stop operation of the printing apparatus to which the processor 27 belongs in the case where the reliability of the registration data is smaller than the predetermined criterion value in the verification result in the verifier 26.

Figure 13:
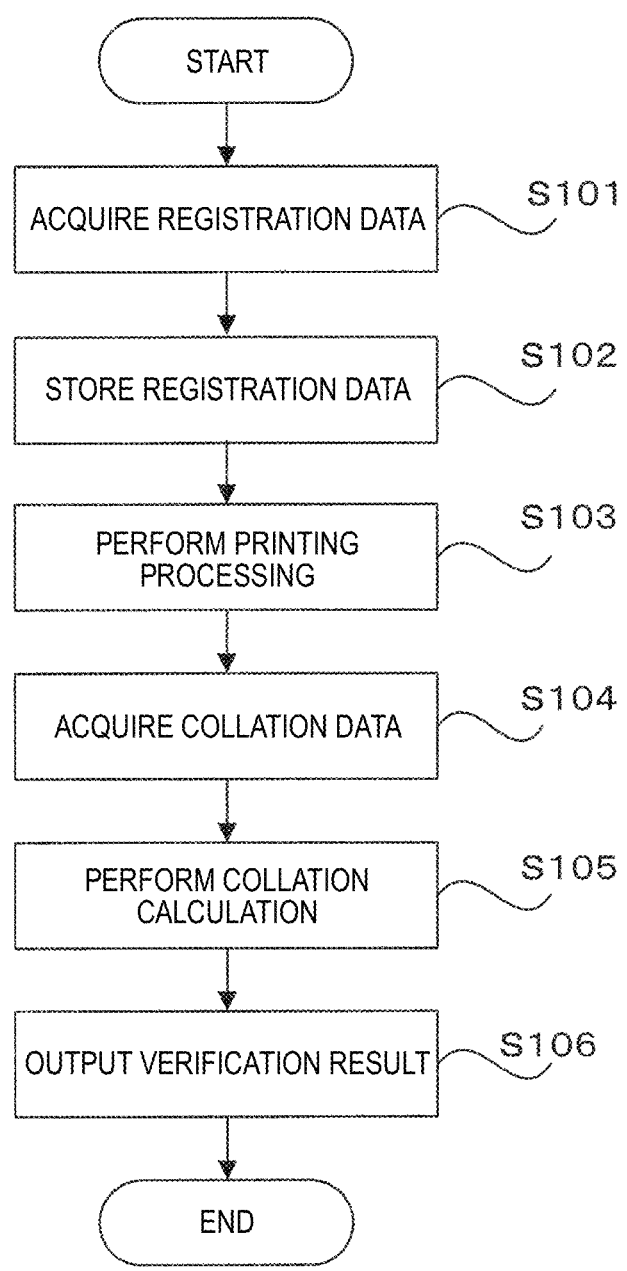
FIG. 13 is a flow chart for explaining a flow of operation of the printing apparatus according to the first exemplary embodiment of the invention.

Next, a flow of the operation of the printing apparatus according to the exemplary embodiment will be described with reference to a flow chart of FIG. 13.

In the printing apparatus according to the exemplary embodiment, when one of tablets 90 fed by the hopper 20 and transported on the transport conveyor 60 is passed directly under the detection camera 30, an image of the tablet 90 is captured by the detection camera 30. The registration data acquirer 22 acquires 32×32 dot registration data from the image captured by the detection camera 30 (step S101).

The registration data acquired by the registration data acquirer 22 is stored in the registration data memory 23 (step S102).

The printing controller 21 grasps a position of the tablet 90 based on the image captured by the detection camera 30, and controls the print head portion 50 which thereby performs printing at a timing when the tablet 90 is passed directly under the print head portion 50 (step S103).

When the tablet 90 on which the printing processing has been performed is passed directly under the inspection camera 40, an image of the tablet 90 is captured after the printing processing by the inspection camera 40. The collation data acquirer 25 acquires 64×64 dot collation data from the image captured by the inspection camera 40 (step S104).

The verifier 26 reads registration data of the same tablet as the acquired collation data from the registration data memory 23, performs collation calculation between the read registration data and the collation data, and verifies whether or not it is possible to obtain determination that the read registration data and the collation data were acquired from the same tablet (step S105). The registration data and the collation data in the collation calculation were acquired from the same tablet. Therefore, when a calculation result that the read registration data and the collation data were acquired from the same tablet can be obtained in the collation calculation, determination can be made that there is a low possibility that wrong determination may occur even if the collation calculation using the registration data is performed in the future.

The verifier 26 outputs the verification result, and the processor 27 executes processing based on the verification result in the verifier 26 (step S106).

Next, a specific calculation method of the collation calculation between the registration data and the collation data will be described in detail with reference to FIGS. 14 to 21.

Incidentally, the calculation method for checking whether the reliability of the registration data is equal to or larger than the predetermined criterion or not will be described in the following description. However, a similar calculation method can be also used when collation calculation is performed between collation data acquired from an object whose identity is to be discriminated, and registration data which has been stored in advance.

First, FIG. 14 shows the example of the registration data and the example of the collation data which are targets of collation calculation. The collation data is data acquired from a region including a region from which the registration data has been acquired. Accordingly, when the collation data and the registration data are acquired from the same object, data corresponding to the registration data should be included in the collation data.

Therefore, as shown in FIG. 15, data having same size as the registration data is sequentially cut out of the collation data, and correlation value calculation is performed.

The correlation value calculation is performed based on the following expression (1). In the following expression (1), a set of the registration data is designated by F; a pixel value of each of pixels of the registration data, $f_i$; a total pixel number of the registration data (and each of the cut regions of the collation data), N (N=32×32=1024); the data of the cut region of the collation data, G; a pixel value of each of pixels of the cut region of the collation data, $g_i$; an average of the pixel values of the respective pixels of the registration data, $f_{AVE}$; and an average of the pixel values of the respective pixels of the cut region of the collation data, $g_{AVE}$.

$$F = \{f_i\}_{i=0}^{N-1} \quad G = \{g_i\}_{i=0}^{N-1} \tag{1}$$

$$\text{Correlation Value} = \frac{\sum_{n=0}^{N-1}(f_n - f_{AVE})(g_n - g_{AVE})}{\sqrt{\sum_{n=0}^{N-1}(f_n - f_{AVE})^2}\sqrt{\sum_{n=0}^{N-1}(g_n - g_{AVE})^2}}$$

Figure 16:
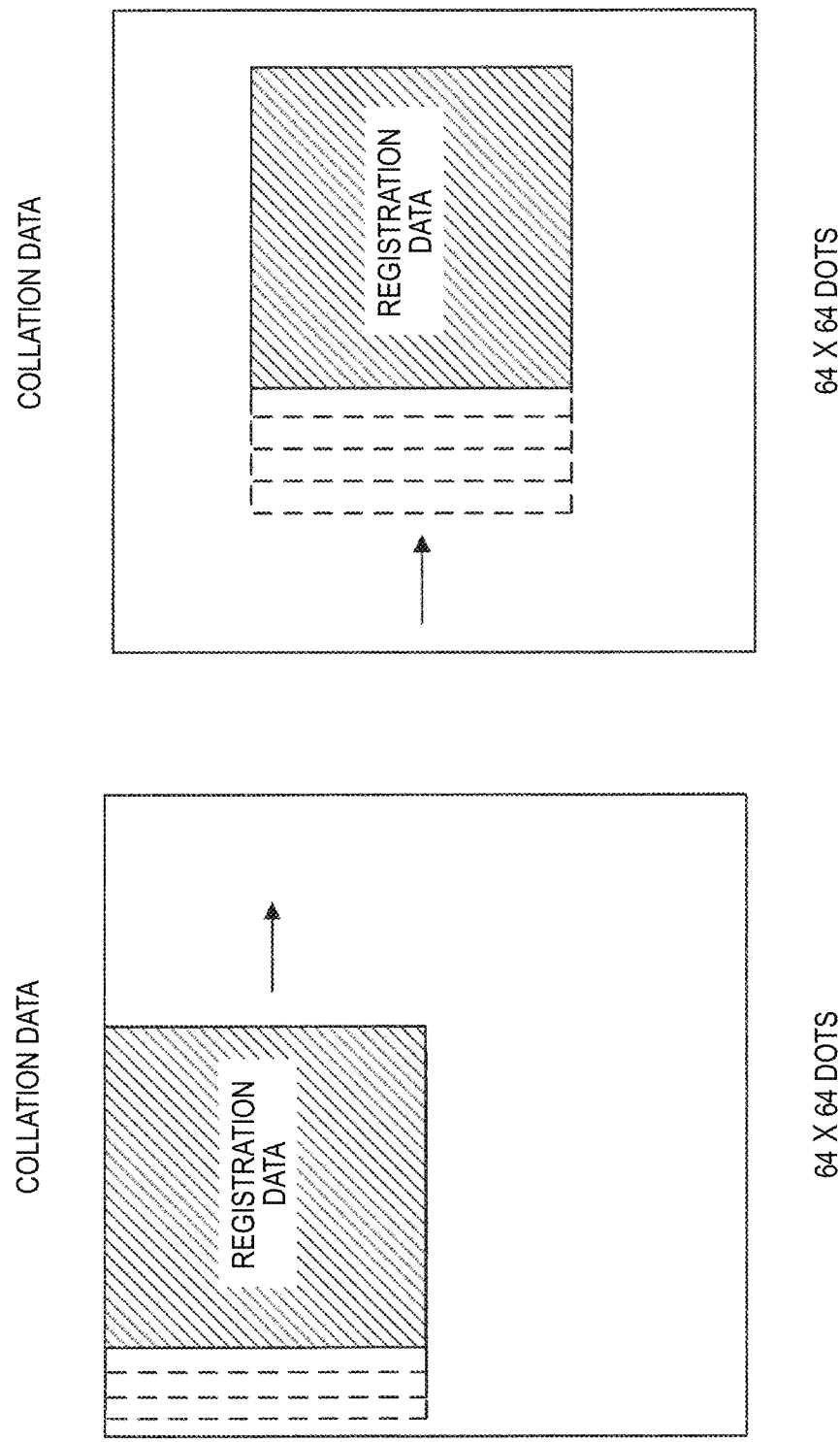
FIG. 16 is a view for explaining a state in which a correlation value is calculated between the registration data and the data cut out of the collation data repeatedly whenever a position where the data is cut out of the collation data is sequentially shifted by one dot (pixel) in an X direction and a Y direction.

A correlation value is calculated between the aforementioned registration data and data cut out of the collation data repeatedly whenever a position where the data is cut out of the collation data is sequentially shifted by one dot (pixel) in an X direction and a Y direction, as shown in FIG. 16.

As a result, by collation calculation performed between one registration data (32×32 dots) and the collation data (64×64 dots), 1,089 ((64−32+1)×(64−32+1)) correlation values can be obtained.

Figure 17:
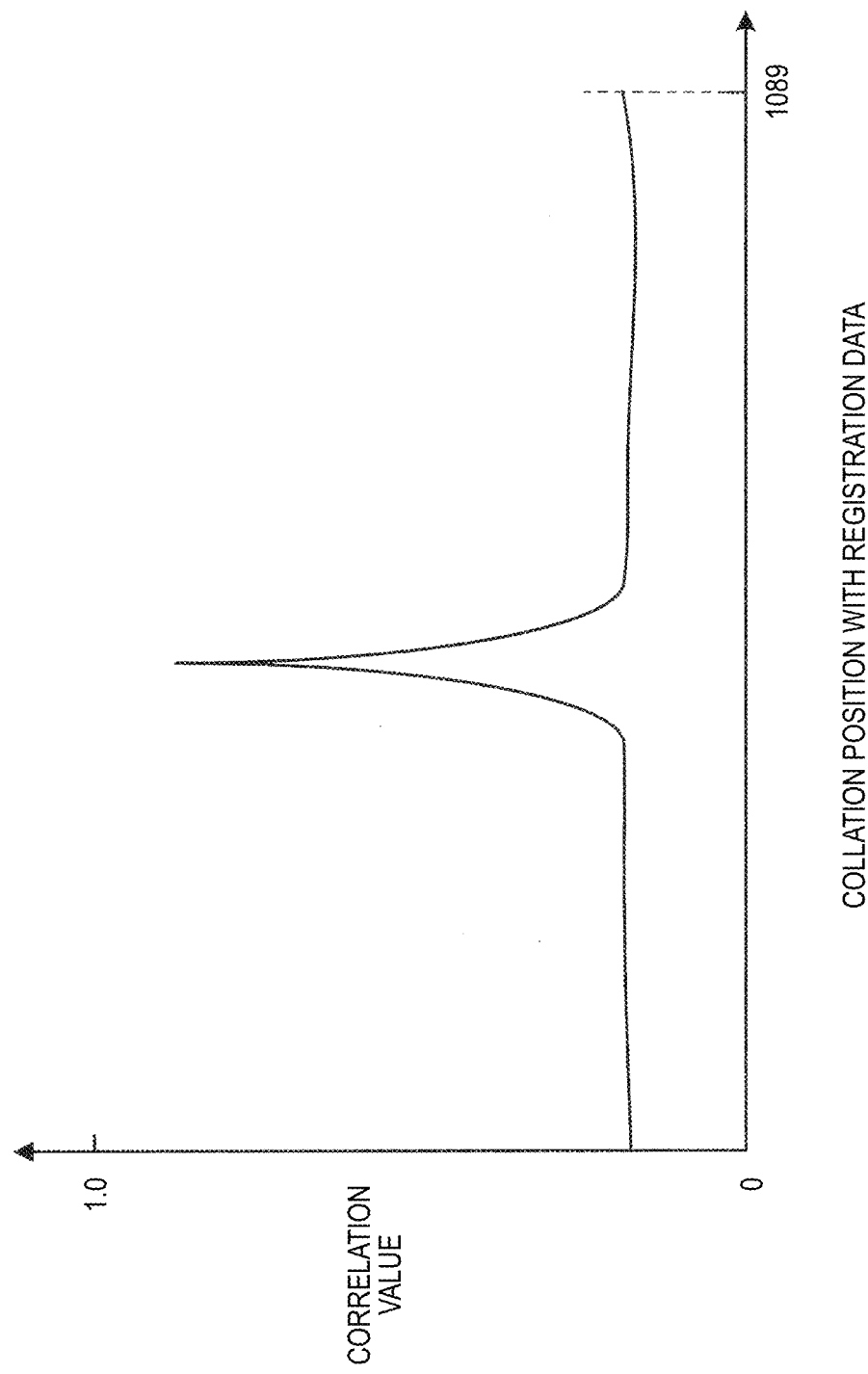
FIG. 17 is a view showing an example in which 1,089 correlation values obtained by the collation calculation are graphed.

FIG. 17 shows an example in which the 1,089 correlation values obtained thus are graphed with respect to positions at which collation with the registration data has been performed in the collation data.

In the example shown in FIG. 17, it can be known that a correlation value between data at a certain position in the collation data and the registration data is a value close to 1, which is larger than at any other place.

That is, in the example shown in FIG. 17, it is possible to determine that the registration data and the collation data were acquired from the same object.

When such a correlation value is obtained in the collation calculation, it is possible to determine that the acquired registration data is reliable enough to be subjected to collation calculation.

However, there may be considered cases where normal registration data cannot be acquired due to various factors such as an illumination quantity when the registration data is acquired, failure in focus setting of the detection camera 30, and a fluctuation in distance between the detection camera 30 and the transport conveyor 60 due to vibration.

Figure 18:
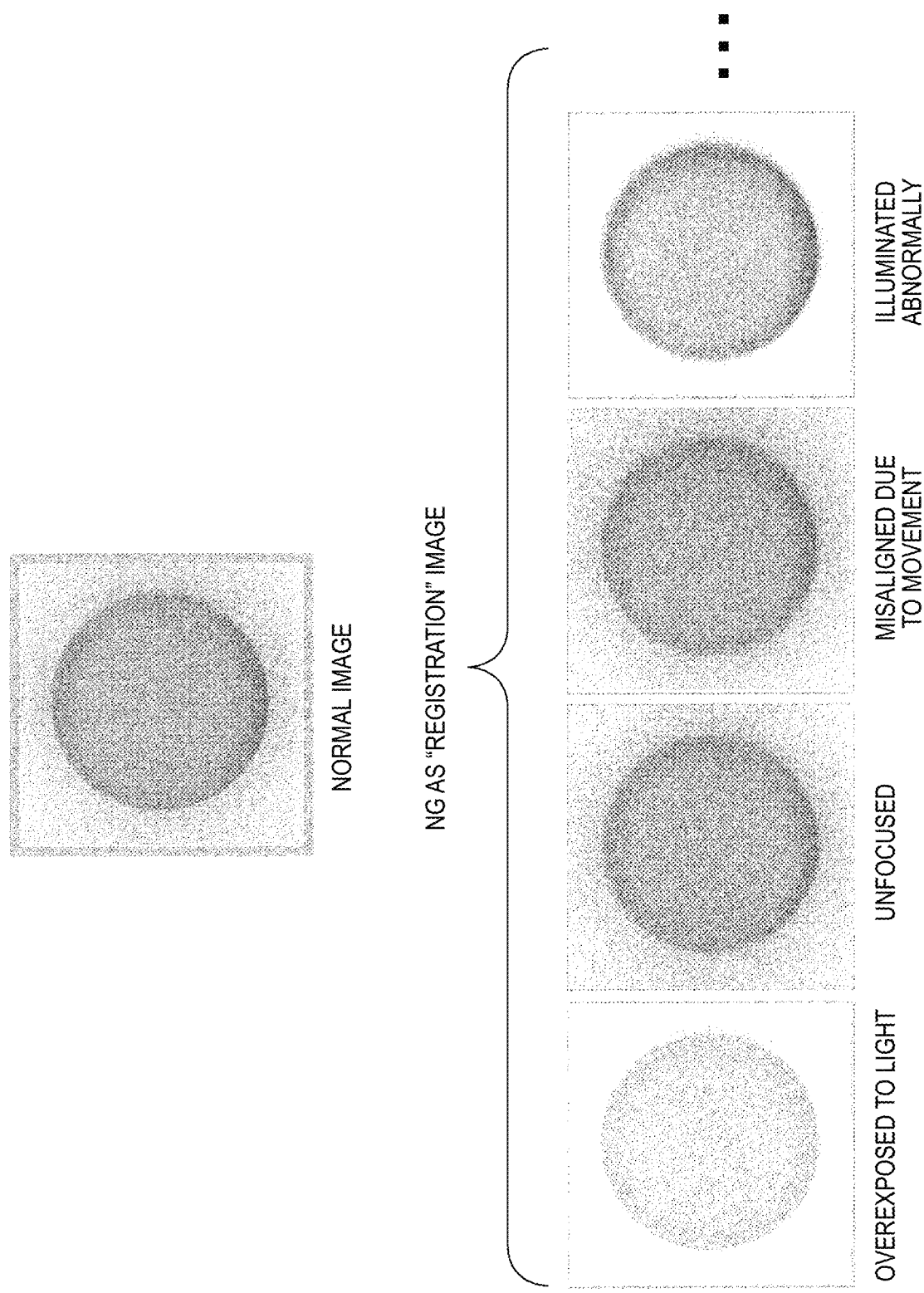
FIG. 18 is a view showing tablet image examples from which normal registration data cannot be acquired.

FIG. 18 shows tablet image examples from which the normal registration data cannot be acquired thus. For example, tablet images captured in cases where the tablet is overexposed to light, unfocused, misaligned due to movement, illuminated abnormally, etc. are shown in FIG. 18. When a captured tablet image is one of such images, the acquired registration data is not normal but there is a high possibility that wrong determination may occur even when collation calculation is performed.

Therefore, in the exemplary embodiment, the reliability of the registration data is not verified by use of only the maximum of the correlation values, but the maximum of the correlation values and the normalized score of the maximum of the correlation values are calculated and the reliability of the registration data is verified by use of the two values.

The normalized score means a feature amount expressing a distribution state of the correlation values. The normalized score of the maximum of the correlation values is calculated based on the following expression (2).

Normalized Score=(Maximum of Correlation Values−Average of Correlation Values)÷Standard Deviation of Correlation Values (2)

The normalized score is an index indicating how far a value in question is from an average of a population. Therefore, the normalized score of the maximum of the correlation values is an index indicating how far the maximum of the 1,089 correlation values is from the average of the correlation values.

Figure 19:
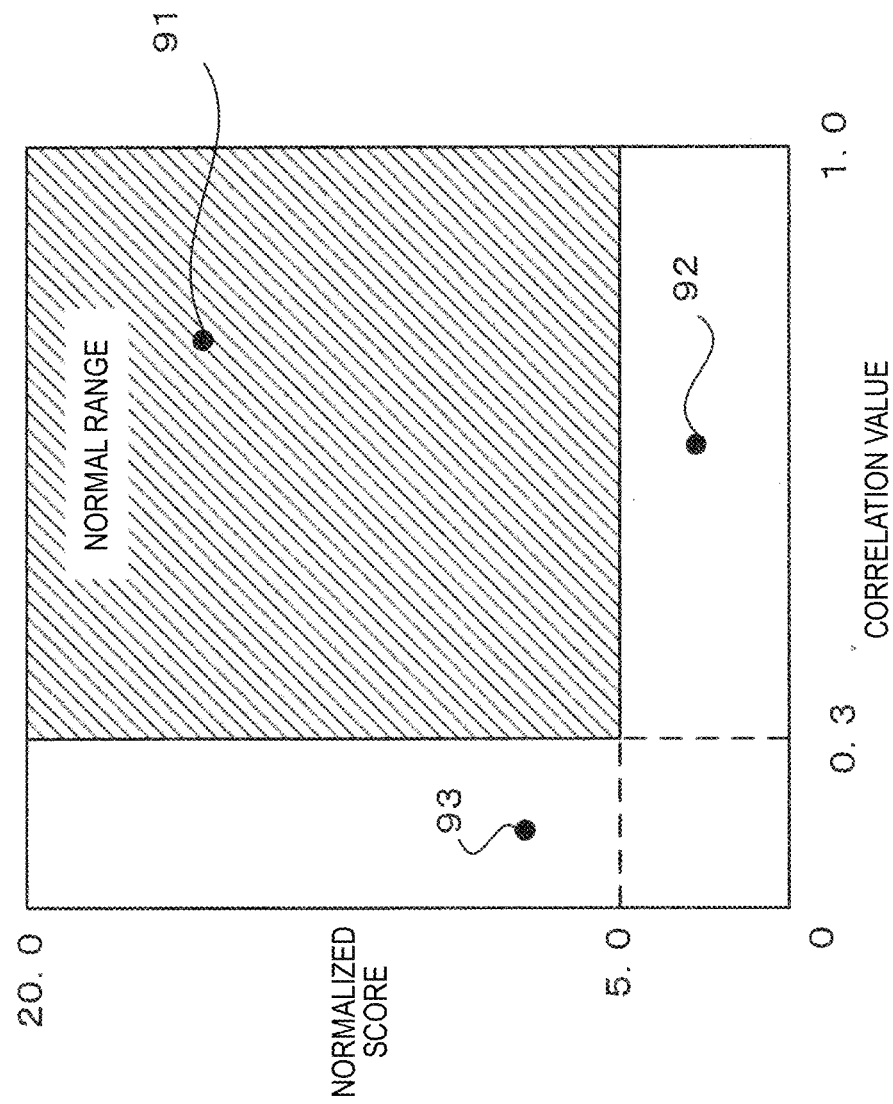
FIG. 19 is a view showing an example of a graph of a maximum of correlation values and a normalized score of the maximum of the correlation values, showing a range where registration data can be regarded as high in reliability.

In the exemplary embodiment, when, for example, the maximum of the correlation values is equal to or larger than 0.3 and the normalized score of the maximum of the correlation values is equal to or larger than 5.0, as shown in FIG. 19, the verifier 26 determines that the registration data can be determined with reliability high enough to be subjected to collation calculation.

That is, assume that the maximum of the correlation values and the normalized score thereof are plotted on the graph shown in FIG. 19. When a plot value in this case falls into a hatched area, the verifier 26 determines that the reliability of the registration data is high. When a plot value in this case falls out of the hatched area, the verifier 26 determines that the reliability of the registration data is low.

For example, in the graph shown in FIG. 19, a plot value 91 indicates that the reliability of the registration data is high, and plot values 92 and 93 indicate that the reliability of the registration data is low.

Figure 20:
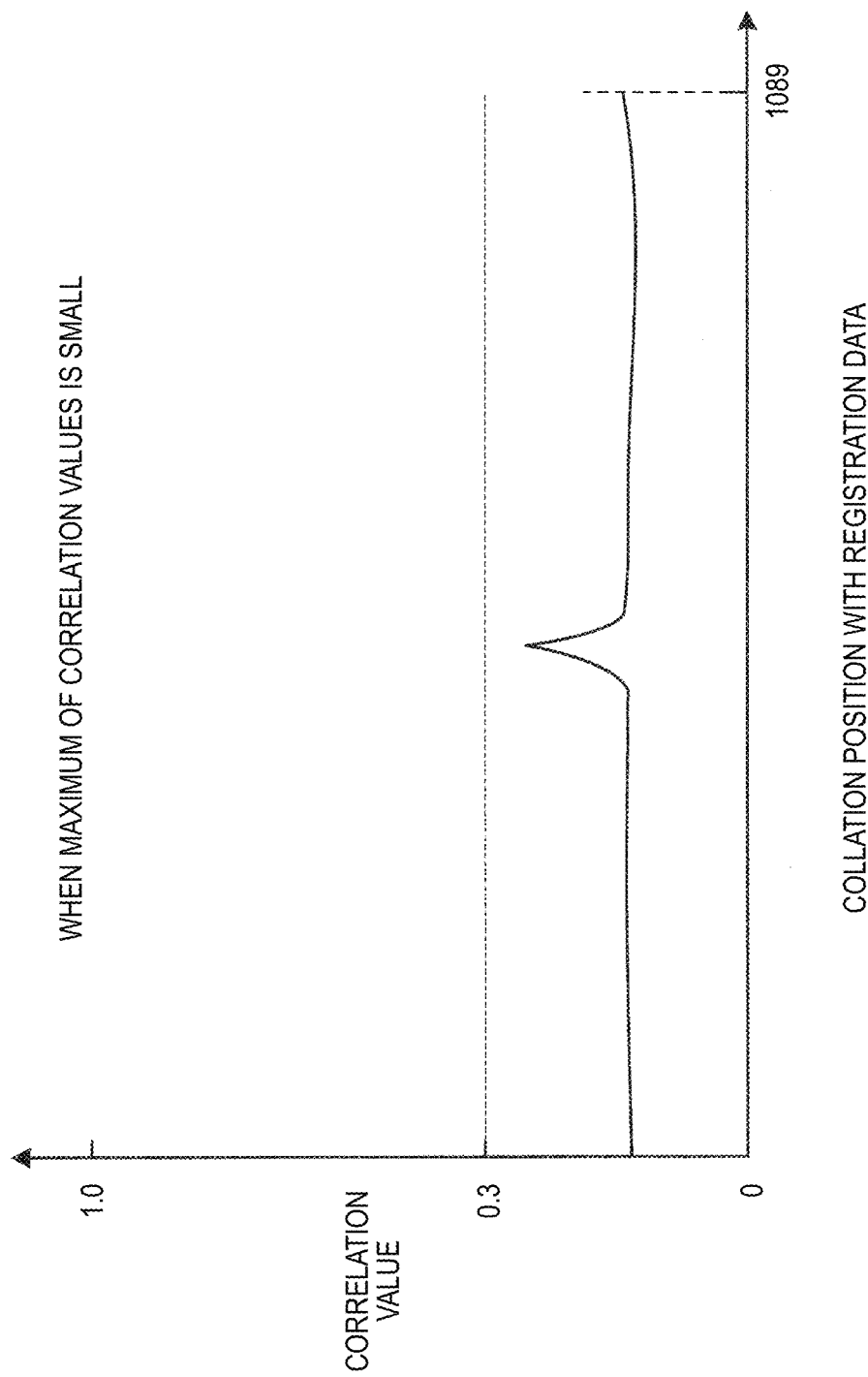
FIG. 20 is a view showing an example of a graph of correlation values in which a maximum of the correlation values is small.
Figure 21:
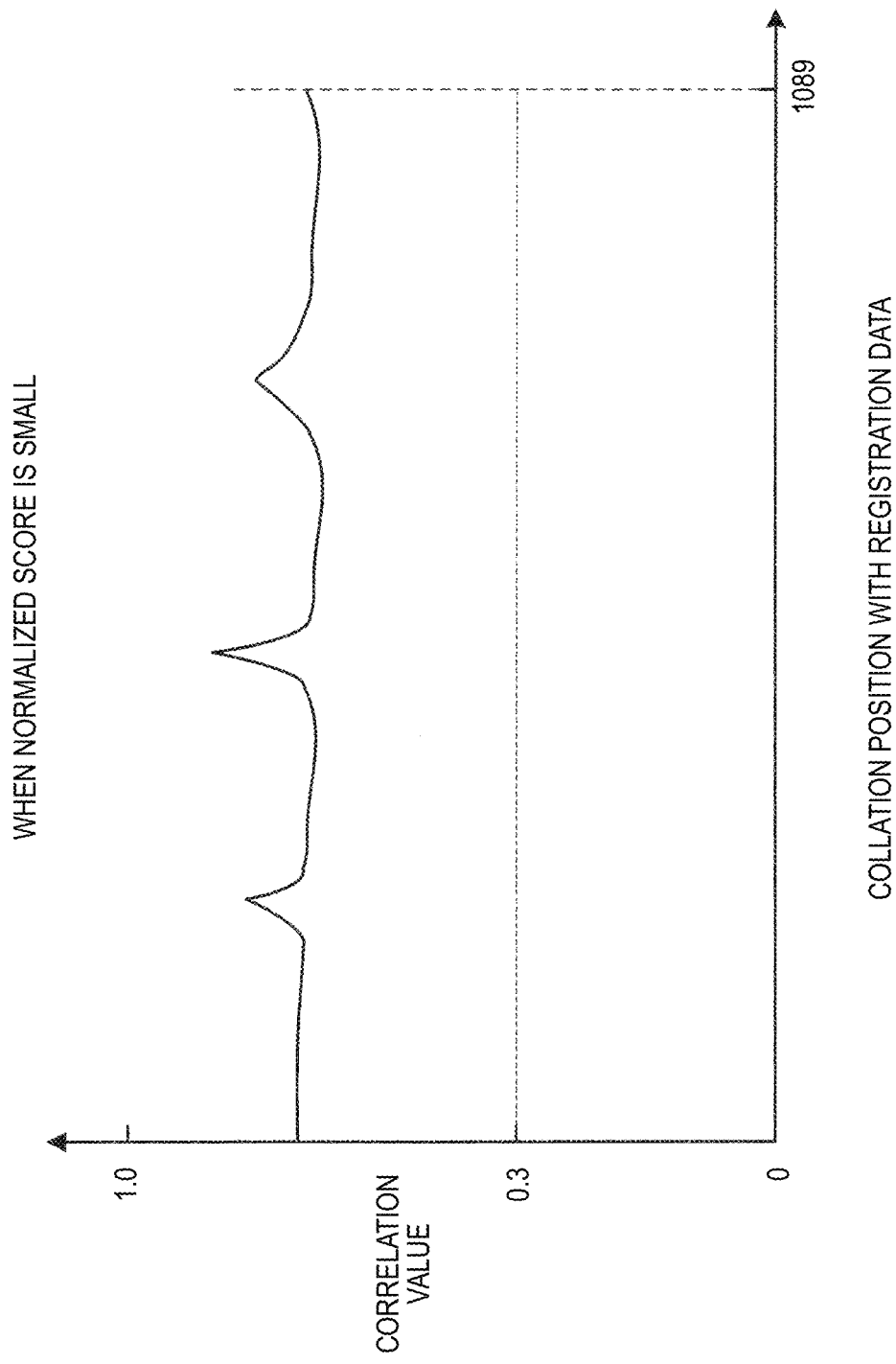
FIG. 21 is a view showing an example of a graph of correlation values in which registration data is not normal in spite of a maximum of the correlation values equal to or larger than a criterion value.

FIG. 20 shows an example of a graph of correlation values in which a maximum of the correlation values is small. FIG. 21 shows an example of a graph of correlation values in which registration data is not normal in spite of a maximum of the correlation values equal to or larger than a criterion value.

In the example of the graph shown in FIG. 20, the maximum of the correlation values does not satisfy the criterion of 0.3. Accordingly, the registration data cannot be determined with high reliability even when collation calculation is performed thereon.

In addition, in the example of the graph shown in FIG. 21, the maximum of the correlation values exceeds the criterion of 0.3, but the correlation values at the other collation positions are also large on the whole. This indicates that a large correlation value can be always obtained when collation calculation is performed at any collation position. Therefore, there is a high possibility that the registration data cannot be determined with high reliability even when collation calculation is performed thereon. When the normalized score of the maximum of the correlation values is calculated in such a case, the value of the normalized score is small. Accordingly, the reliability of such registration data can be verified accurately by use of not only the maximum of the correlation values but also the normalized score of the maximum of the correlation values.

Second Exemplary Embodiment

Next, a printing apparatus according to a second exemplary embodiment of the invention will be described.

The printing apparatus according to the exemplary embodiment has a similar configuration to that of the aforementioned printing apparatus according to the first exemplary embodiment. Therefore, description will be made only on the configuration which is different from that of the printing apparatus according to the first exemplary embodiment.

Figure 22:
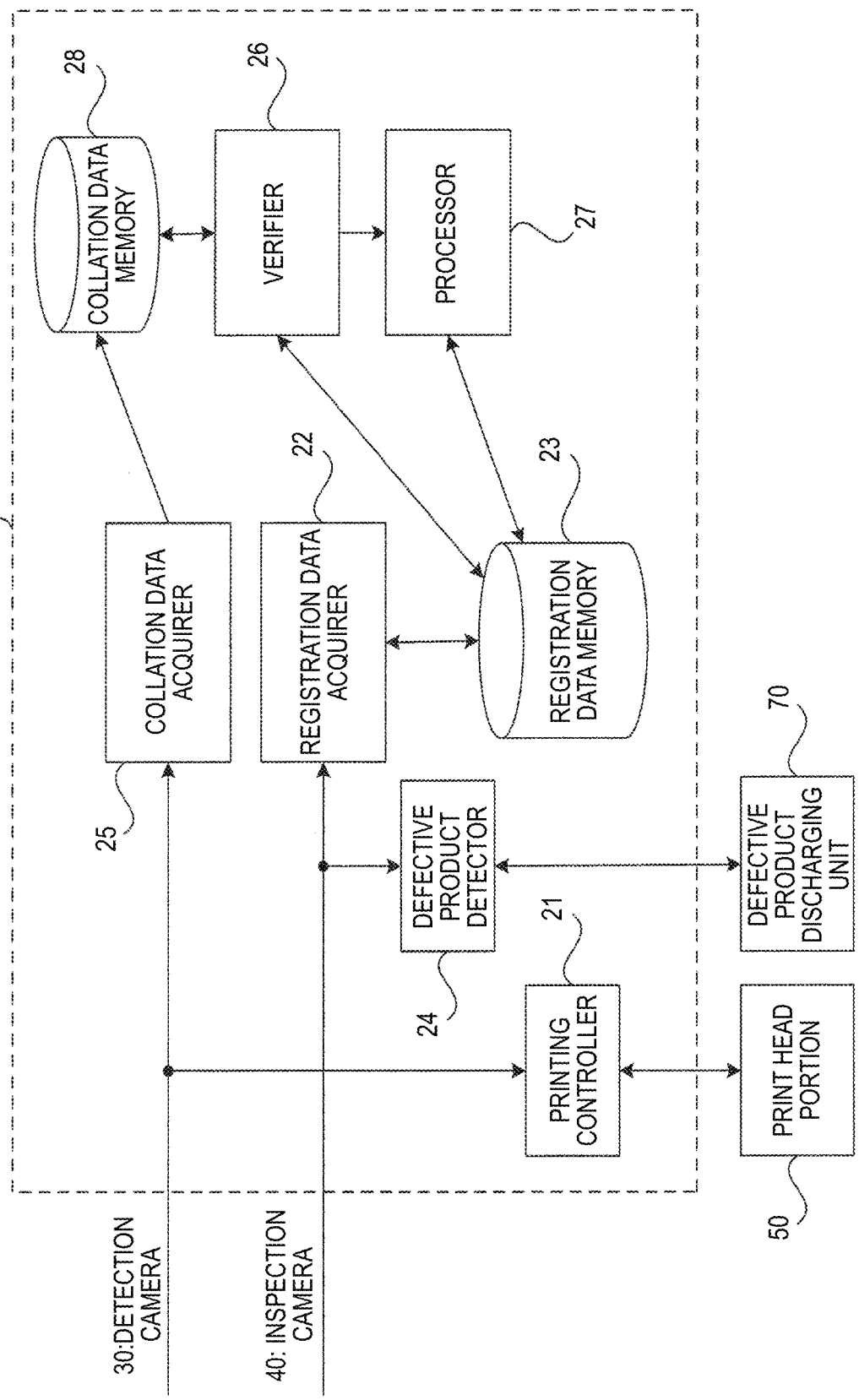
FIG. 22 is a block diagram showing a functional configuration of a controller 10a in a second exemplary embodiment of the invention.

The printing apparatus according to the exemplary embodiment has a configuration in which the controller 10 in the printing apparatus according to the first exemplary embodiment shown in FIG. 3 is replaced with a controller 10a shown in FIG. 22.

In the controller 10a in the exemplary embodiment, a collation data memory 28 is added to the controller 10 in the first exemplary embodiment shown in FIG. 3.

In addition, in the controller 10a in the exemplary embodiment, a collation data acquirer 25 acquires feature data as 64×64 dot collation data from an image captured by a detection camera 30, the feature data representing a feature distributed in a second region of a predetermined size on a tablet 90.

The collation data memory 28 temporarily stores the collation data acquired by the collation data acquirer 25.

Further, in the controller 10a in the exemplary embodiment, a registration data acquirer 22 acquires feature data as 32×32 dot registration data from an image of the tablet 90 which is captured after printing processing by an inspection camera 40, the feature data representing a feature distributed in a first region of a predetermined size on a front surface of the tablet 90.

That is, in the printing apparatus according to the exemplary embodiment, the collation data which is acquired from an image of the tablet 90 captured initially by the detection camera 30 is stored once. The registration data is acquired from an image of the tablet 90 captured after the printing processing by the inspection camera 40, and reliability of the registration data is checked by use of the collation data stored in advance.

Incidentally, in the printing apparatus according to the exemplary embodiment, the registration data is acquired from the image including the tablet 90 after the printing. Accordingly, the whole image of the tablet after the printing may be stored as the registration data when there is an empty space in memory capacity of a registration data memory 23.

Thus, according to the aforementioned two exemplary embodiments, i.e. the first exemplary embodiment and the second exemplary embodiment, the collation data acquirer 25 acquires the collation data from one of the image captured by the detection camera 30 and the image captured by the inspection camera 40. Moreover, the registration data acquirer 22 acquires the registration data from the other of the image captured by the detection camera 30 and the image captured by the inspection camera 40.

Figure 23:
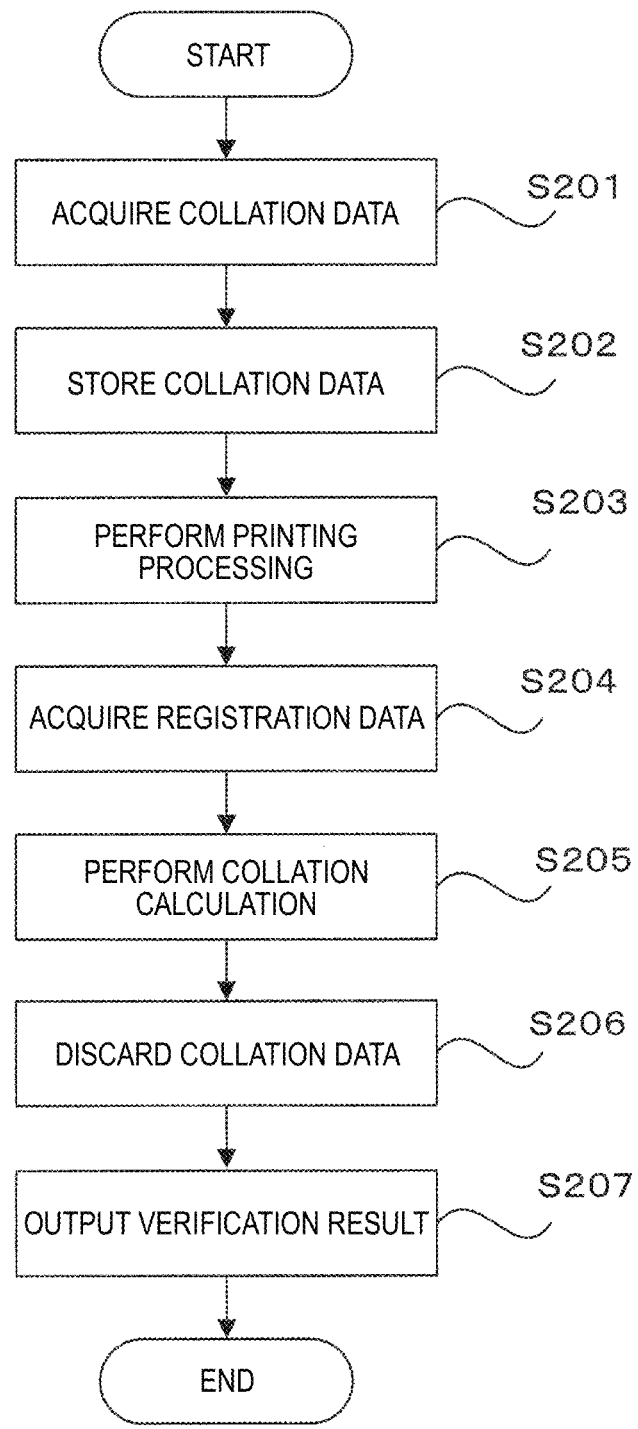
FIG. 23 is a flow chart for explaining a flow of operation of a printing apparatus according to the second exemplary embodiment of the invention.

Next, a flow of operation of the printing apparatus according to the exemplary embodiment will be described with reference to a flow chart of FIG. 23.

In the printing apparatus according to the exemplary embodiment, when one of tablets 90 fed by a hopper 20 and transported on a transport conveyor 60 is passed directly under the detection camera 30, an image of the tablet 90 is captured by the detection camera 30. The collation data acquirer 25 acquires 64×64 dot collation data from the image captured by the detection camera 30 (step S201).

The collation data acquired by the collation data acquirer 25 is stored in the collation data memory 28 (step S202).

A printing controller 21 grasps a position of the tablet 90 based on the image captured by the detection camera 30, and controls a print head portion 50 which thereby performs printing on the tablet 90 at a timing when the tablet 90 is passed directly under the print head portion 50 (step S203).

When the tablet 90 on which the printing processing has been performed is passed directly under the inspection camera 40, an image of the tablet 90 is captured after the printing processing by the inspection camera 40. The registration data acquirer 22 acquires 32×32 dot registration data from the image captured by the inspection camera 40 (step S204).

A verifier 26 reads collation data of the same tablet as the acquired registration data from the collation data memory 28, performs collation calculation between the read collation data and the registration data, and verifies whether determination can be made that the read collation data and the registration data were obtained from the same tablet or not (step S205). That is, the registration data and the collation data in the collation calculation were acquired from the same tablet. Accordingly, as long as it is possible to obtain a calculation result that the registration data and the collation data were acquired from the same tablet in the collation calculation, determination can be made that there is a low possibility that wrong determination may occur even if collation calculation using the registration data is performed in the future.

When the collation calculation is completed, the collation data used for the collation calculation is discarded (step S206). The verifier 26 outputs a verification result in the collation calculation, and a processor 27 executes processing based on the verification result in the verifier 26 (step S207).

In the processing apparatus according to the exemplary embodiment, the registration data is acquired from the image of the tablet after the printing processing. Accordingly, the processor 27 may perform character recognition processing of information printed on the tablet after the printing, and store the character information obtained by the character recognition processing into the registration data memory 23.

In this manner, the registration data memory 23 stores the character information obtained by the character recognition processing of the verifier 26, together with the registration data.

Figure 24:
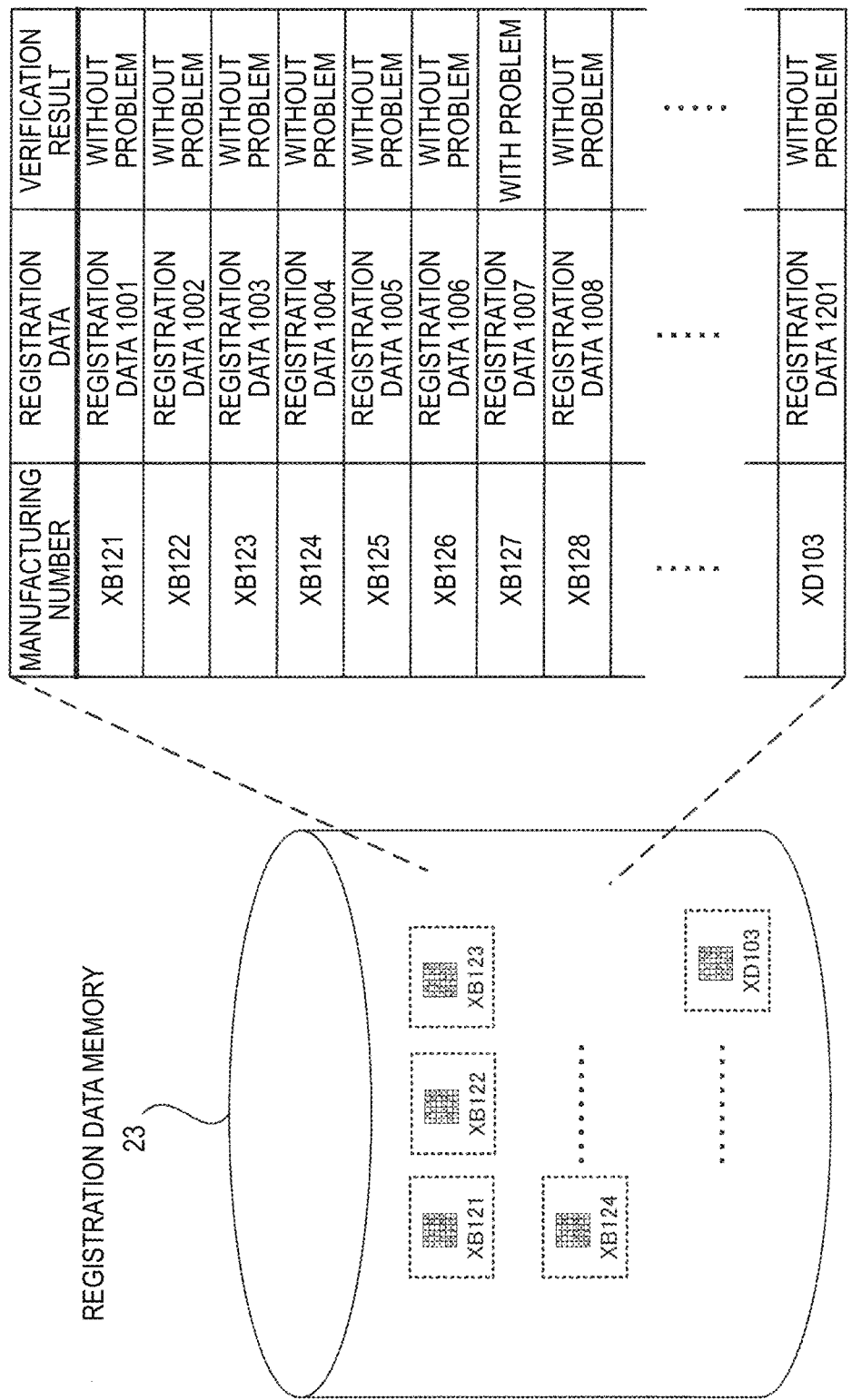
FIG. 24 is a view showing an example in which information pieces about manufacturing numbers different from one tablet from another are stored together with registration data acquired from the tablets respectively.
Figure 25:
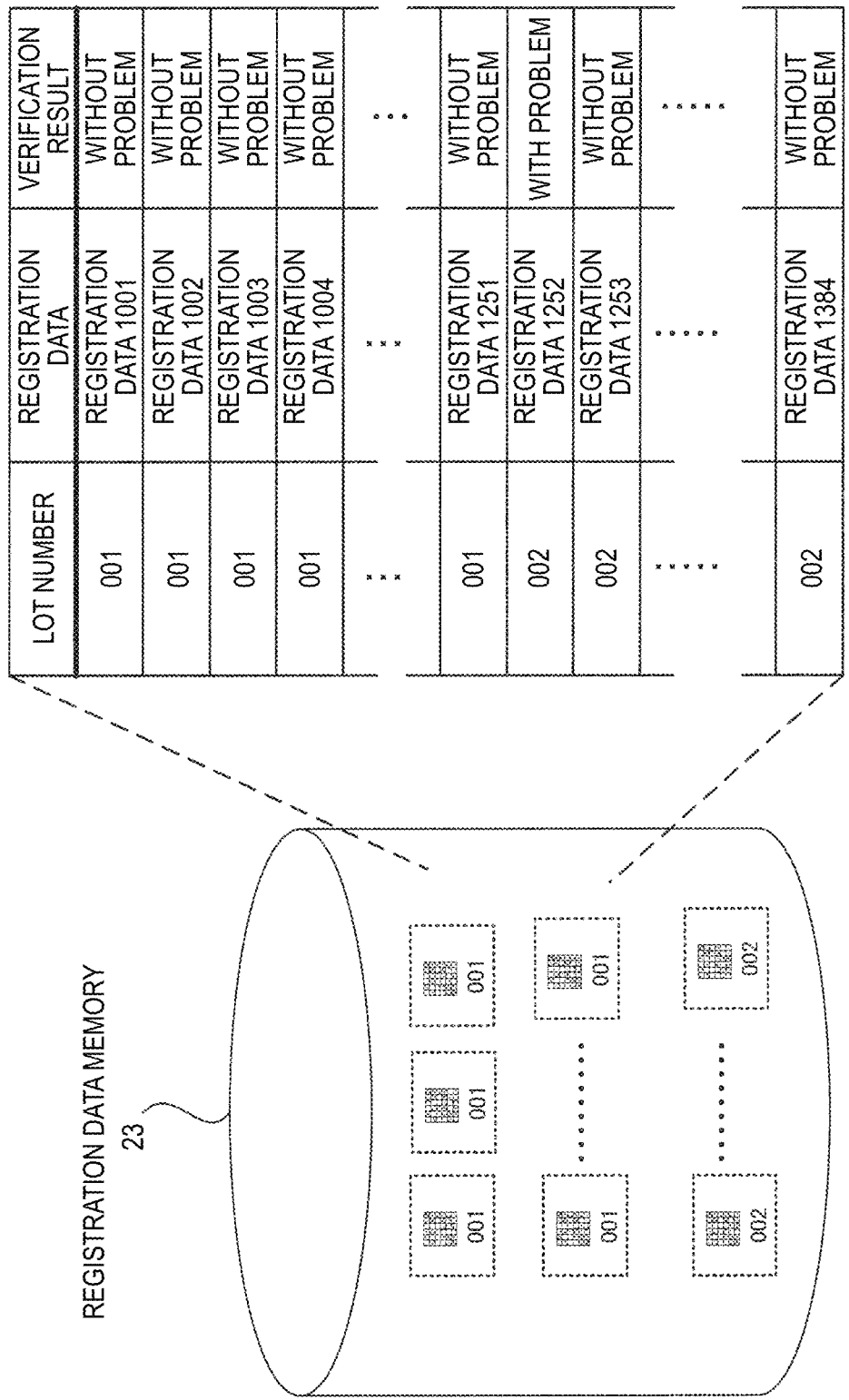
FIG. 25 is a view showing an example in which an information piece about a lot number for specifying a production unit (lot) with which each tablet was manufactured is stored together with registration data acquired from the tablet.

FIG. 24 and FIG. 25 show examples of the registration data memory 23 which are designed to store the character information together with the registration data by such processing.

In the example shown in FIG. 24, an example in which information pieces about manufacturing numbers differing from one tablet to another are stored together with registration data acquired from the tablets respectively. Thus, registration data of each tablet is stored together with an information piece like a manufacturing number by which the tablet can be specified uniquely. With this configuration, it will go well if collation calculation is performed once in order to discriminate genuineness of any tablet available on the market.

In addition, FIG. 25 shows an example in which an information piece about a lot number for specifying a production unit (lot) with which each tablet was manufactured is stored together with registration data acquired from the tablet. Thus, registration data of each tablet is stored together with an information piece like a lot number for specifying a lot with which the tablet was manufactured. With this configuration, in order to discriminate genuineness of any tablet available on the market, it will go well if collation calculation is performed a number of times corresponding to the number of tablets in the lot to which the tablet belongs.

[Reason Why Data Acquisition Region is Determined Based on Both External Shape of Tablet and Printing Pattern]

In the aforementioned first and second exemplary embodiments, as described above, the registration data acquirer 22 determines a position of a registration data acquisition region 81 based on a position defined by an external shape of a tablet to be registered and a position of a printing pattern printed on the tablet, from an image including the tablet. In addition, the collation data acquirer 25 similarly determines a position of a collation data acquisition region 82 based on a position defined by the external shape of the tablet and the position of the printing pattern printed on the tablet, from an image including the tablet. The reason why the position of the registration data acquisition region 81 and the position of the collation data acquisition region 82 are determined thus will be described below.

First, in an object having an inclined surface like a circular tablet, a shadow (intensity of a shade) generated due to fine surface unevenness by a surface light source such as the ring illumination unit 31, 41 changes largely from place to place.

For example, when light emitted from the ring illumination unit 31 (41) is radiated onto the circular tablet as shown in (A) of FIG. 26, the shade appears weakly at a central portion of the tablet but appears intensely at a peripheral portion of the tablet. That is, an information amount of a random pattern at the peripheral portion is larger than that at the central portion.

It can be known that the information amount of the random pattern is larger as it goes from the central portion of the tablet toward the peripheral portion thereof, for example, as in an example shown in (B) of FIG. 26.

Therefore, when registration data is acquired from the object such as the circular tablet, it is desirable that the position of the registration data acquisition region 81 is set at the peripheral portion of the object if possible.

However, when characters etc. are printed on the object and the position of the registration data acquisition region 81 is defined based on the characters etc., a problem arises if printing misalignment etc. occurs.

When printing is performed on the object such as the tablet, the printing is performed on the object during transport. Therefore, the printing pattern is not always located at a fixed position relative to the shape of the object. Therefore, when the position of the registration data acquisition region 81 is defined based on the printing pattern, normal registration data may not be able to be acquired in some cases if printing misalignment occurs.

Figure 27:
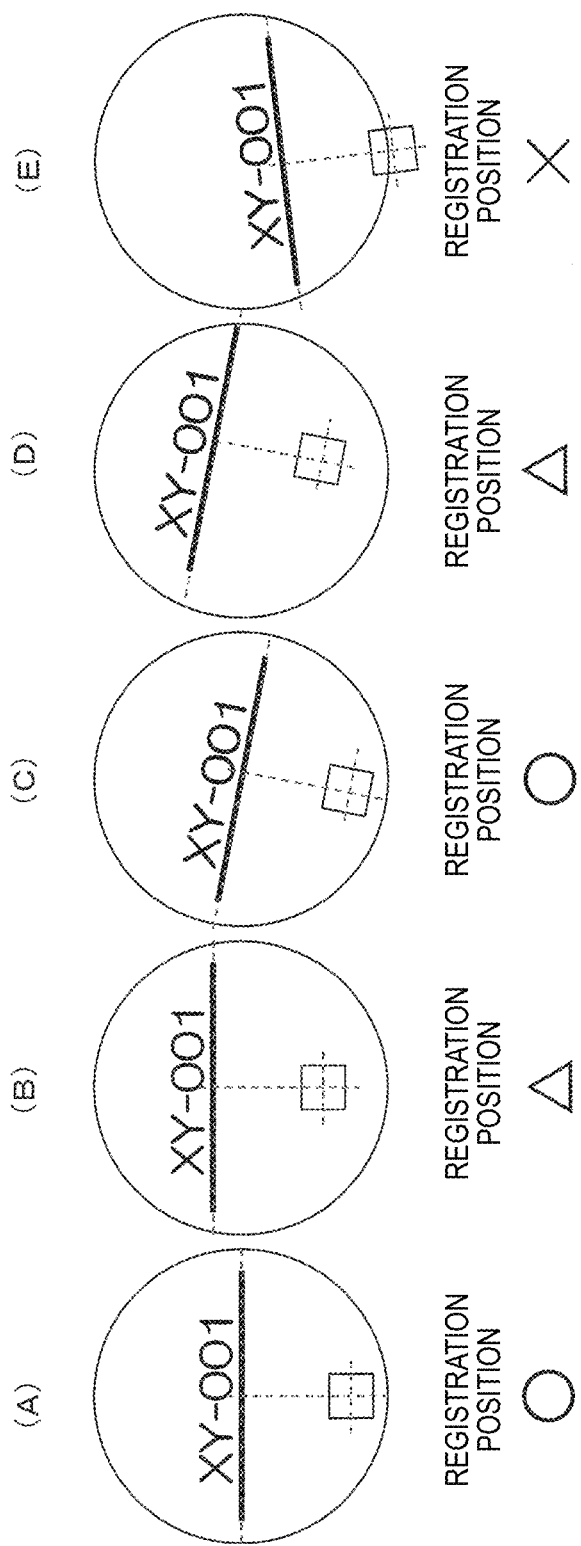
FIG. 27 is a view showing examples (A), (B), (C), (D) and (E) of a case where a registration data acquisition region is determined based on only a printing pattern.

For example, FIG. 27 shows an example in which how the registration data acquisition region changes if printing misalignment occurs in a case where characters "XY-001" and a horizontal line are printed on the circular tablet.

In this FIG. 27, a case where a perpendicular bisector of the horizontal line is virtually drawn on the tablet and a point on the perpendicular bisector at a fixed distance from the horizontal line is defined as the center of the registration data acquisition region is shown.

In such a case, the registration data acquisition region is set at an appropriate position when the printing pattern is printed normally, as shown in (A) of FIG. 27.

In addition, even when the printing pattern is slightly tilted in terms of direction as shown in (C) of FIG. 27, the registration data acquisition region is set at an appropriate position.

However, when the printing pattern is displaced from the center and printed as shown in (B) or (D) of FIG. 27, the registration data acquisition region cannot be set at an appropriate position.

Further, when the printing pattern is displaced greatly from the center and printed as shown in (E) of FIG. 27, the registration data acquisition region is set out of the external shape of the tablet so that the registration data acquisition region cannot be set at a position where registration data can be acquired normally.

Therefore, the registration data acquirer 22 in the printing apparatus according to the exemplary embodiment determines the position of the registration data acquisition region 81 for acquiring the registration data based on the position defined by both the external shape of the tablet and the position of the printing pattern (printing information) printed on the tablet.

Specifically, the registration data acquirer 22 determines the position of the registration data acquisition region 81 by the following procedure, as shown in (A) of FIG. 28.

(1) Draw a line segment which extends from the horizontal line (line) in the printing pattern to a circumferential portion (edge portion) of the tablet, (2) Extend a perpendicular bisector of the drawn line segment to a side where the characters "XY-100" are not printed with respect to the horizontal line, (3) Obtain a position of an intersection point between the perpendicular bisector and the circumferential portion of the tablet, (4) Move a preset distance d from the intersection point toward the center of the tablet along the perpendicular bisector, and (5) Determine a registration data acquisition region 81 in which an arrival point on the perpendicular bisector moved by the distance d from the intersection point serves as center coordinates.

In addition, also when the collation data acquirer 25 acquires collation data or when collation data is acquired from a tablet whose genuineness is to be discriminated, the position of the collation data acquisition region 82 is determined by a similar procedure, as shown in (B) of FIG. 28.

When the position of the registration data acquisition region 81 is determined thus based on both the external shape of the tablet and the printing pattern, description about how the registration data acquisition region 81 changes if printing misalignment occurs will be made with reference to FIG. 29.

Figure 29:
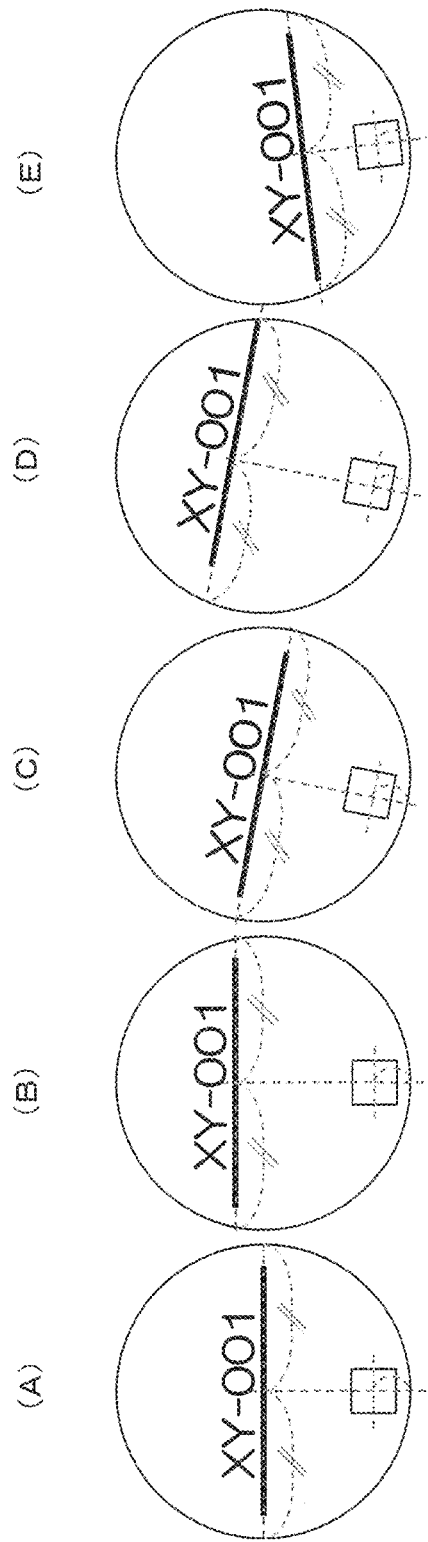
FIG. 29 is a view showing examples (A), (B), (C), (D) and (E) of a case where the registration data acquisition region is determined based on both an external shape of a tablet and a printing pattern.

When the printing pattern is normally printed as shown in (A) of FIG. 29, it is a matter of course that the registration data acquisition region is set at an appropriate position.

In addition, also when the printing pattern is slightly tilted in terms of direction as shown in (C) of FIG. 29, the registration data acquisition region is set at an appropriate position.

Even when the printing pattern is displaced from the center and printed as shown in (B) or (D) of FIG. 29, it can be known that the registration data acquisition region is set at an appropriate position.

Further, even when the printing pattern is displaced greatly from the center and printed as shown in (E) of FIG. 29, it can be known that the registration data acquisition region is set at an appropriate position.

[Genuineness Discriminating Apparatus]

Next, a genuineness discriminating apparatus for determining whether, for example, a tablet which has been collected from the market is a regularly manufactured genuine tablet (authentic object) or a counterfeit tablet will be described with reference to FIG. 30.

Figure 30:
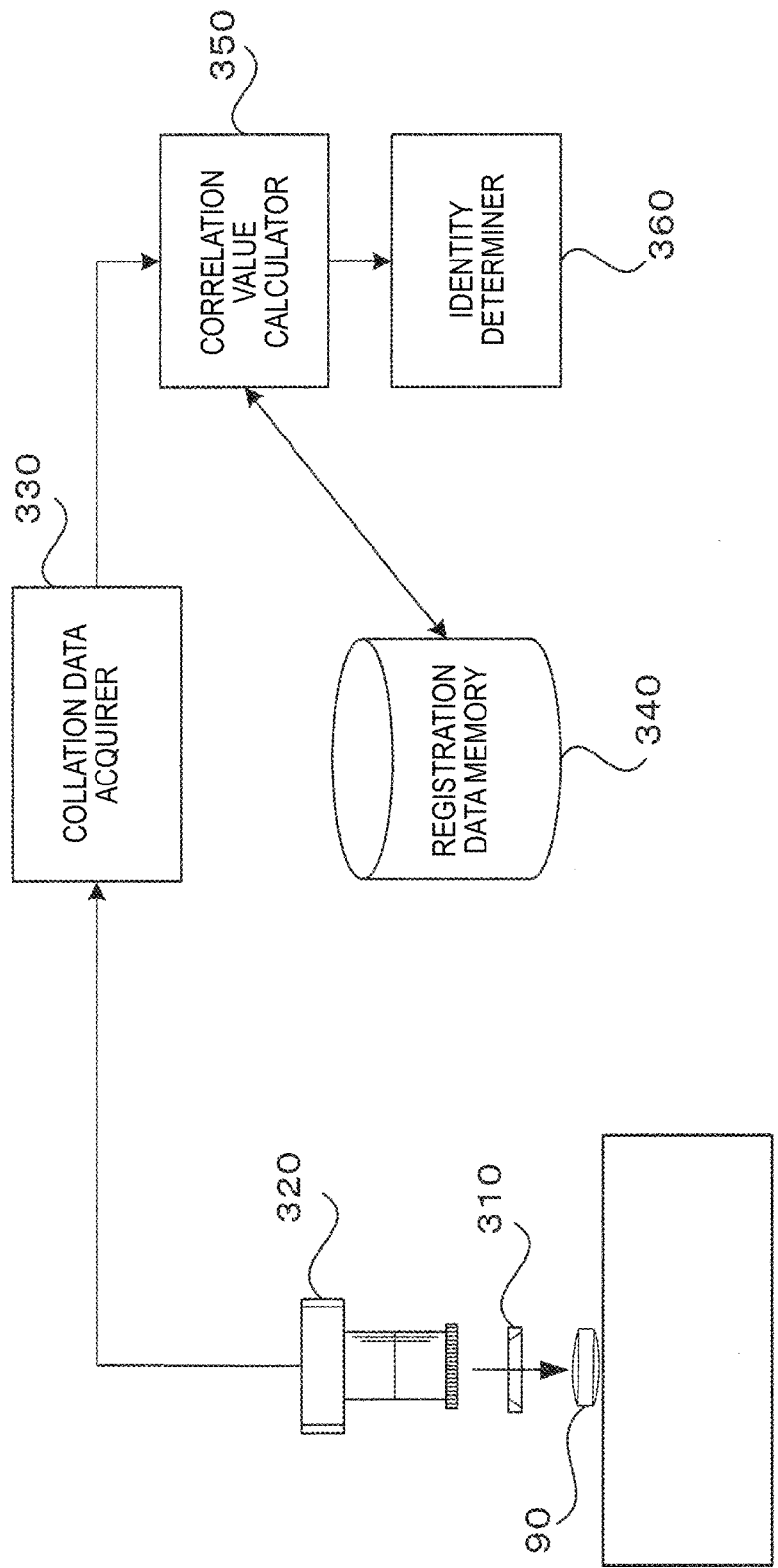
FIG. 30 is a block diagram for explaining a configuration of a genuineness discriminating apparatus 300.

FIG. 30 is a view showing a configuration of an exemplary embodiment of such a genuineness discriminating apparatus 300.

As shown in FIG. 30, the genuineness discriminating apparatus 300 includes a ring illumination unit 310, a camera 320, a collation data acquirer 330, a registration data memory 340, a correlation value calculator 350, and an identity determiner 360.

The ring illumination unit 310 is an illumination device for radiating light onto a tablet 90 serving as a discrimination target on which genuineness discrimination (authenticity discrimination) is performed. The camera 320 is an imager for capturing an image including the tablet serving as the discrimination target.

The collation data acquirer 330 acquires feature data, as collation data, from the image captured by the camera 320, the featuring data representing a feature distributed in a region determined based on a position defined by an external shape of the tablet 90 and a position of a printing pattern printed on the tablet 90.

The registration data memory 340 stores registration data which has been acquired from a genuine tablet (authentic object) and registered in advance. That is, similar data to the data stored in the registration data memory 23 which has been described in the aforementioned first and second exemplary embodiments is stored in the registration data memory 340.

The correlation value calculator 350 performs correlation value calculation between the collation data acquired by the collation data acquirer 330 and the registration data stored in the registration data memory 340. Since the correlation value calculation in the correlation value calculator 350 is a similar calculation method to the calculation method performed in the verifier 26 which has been described in the aforementioned first and second exemplary embodiments, detailed description thereof will be omitted.

The identity determiner 360 compares the collation data acquired by the collation data acquirer 330 with the registration data stored in the registration data memory 340, to thereby determine identity of the tablet serving as the discrimination target. Specifically, the identity determiner 360 determines whether the tablet serving as the discrimination target is same as one of tablets from which registration data stored in the registration data memory 340 have been acquired or not.

That is, when a determination result is obtained that the tablet serving as the discrimination target is same as one of tablets which were manufactured in the past and sold in the market, determination can be made that the tablet serving as the discrimination target is a genuine tablet. On the other hand, when a determination result is obtained that the tablet serving as the discrimination target is not the same as any of the tablets which were manufactured in the past and sold in the market, determination can be made that the tablet serving as the discrimination target is a counterfeit tablet.

[Modification]

In the aforementioned exemplary embodiment, the case where registration data for determining identity of a tablet is acquired and stored when printing processing is performed on a front surface of the tablet by the printing apparatus has been used and described. However, the invention is not limited to such a case. For example, the invention may be also similarly applied in a case where an image of a tablet to be registered is captured and registration data is acquired from the captured image in a data acquiring apparatus which does not perform printing processing.

In addition, the case where printing is performed only on a single side of the tablet has been used and described in the aforementioned exemplary embodiments. However, the invention is not limited thereto. The invention may be also similarly applied in a case of a configuration in which a turnover device for turning over the tablet is provided at the end of the transport conveyor 60, and another set of a detection camera 30, an inspection camera 40, a print head portion 50, etc. is prepared so that printing processing can be also performed on the tablet which has been turned over.

In addition, in order to simplify description, the case where tablets 90 are transported in one line on the transport conveyor 60 in the printing apparatus according to each of the aforementioned exemplary embodiments has been used and described. However, the invention may be also similarly applied in a case where plural lines of tablets are transported simultaneously and printing is performed on the plural tablets simultaneously.

Further, the case where 32×32 dot image data is acquired as the registration data, image data measuring 64 dots by 64 dots is acquired as the collation data, and collation calculation is performed therebetween has been used and described in each of the aforementioned exemplary embodiments. However, the data sizes of the registration data and the collation data are not limited to such sizes.

Although various exemplary embodiments have been described above, these exemplary embodiments may be combined and configured. In addition, the present disclosure is not limited to the aforementioned exemplary embodiments at all but can be carried out in various modes without departing from the gist of the present disclosure.

REFERENCE SIGNS LIST 10, 10a controller
11 CPU
12 memory
13 memory device
14 communication interface (IF)
15 user interface (UI) device
16 control bus
20 hopper
21 printing controller
22 registration data acquirer
23 registration data memory
24 defective product detector
25 collation data acquirer
26 verifier
27 processor
28 collation data memory
29 test data memory
30 detection camera
31 ring illumination unit
40 inspection camera
41 ring illumination unit
50 print head portion
60 transport conveyor
70 defective product discharging unit
71 good product storing box
72 defective product storing box
81 registration data acquisition region
82 collation data acquisition region
90 tablet
90a tablet (printing failure)
91 to 93 plot value
300 genuineness discriminating apparatus
310 ring illumination unit
320 camera
330 collation data acquirer
340 registration data memory
350 correlation value calculator
360 identity determiner

The invention claimed is:

1. A printing apparatus comprising:
a printer that performs printing on an object to be registered;
a CPU configured to:
acquire concentration values of respective pixels in a registration data acquisition region of a predetermined size in a captured image of the object to be registered before the printing as registration data, the registration data acquisition region being determined based on an external shape of the object to be registered and a position of a printing information to be printed on the object to be registered;
acquire concentration values of respective pixels in a collation data acquisition region of a predetermined size in a captured image of the object on which printing has been performed by the printer as collation data, the collation data acquisition region being determined based on a position defined by an external shape of the object and a position of printing information that has been printed on the object; and
calculate correlation values between the registration data and the collation data; and
determine that the object on which printing has been performed is same as the object to be registered before the printing when the correlation value satisfies a predetermined criterion; and
a memory that stores the registration data as data for determining identity of the object.

2. A genuineness discriminating apparatus comprising:
an imager that captures an image including an object to be discriminated; and
a CPU configured to:
acquire concentration values of respective pixels in a collation data acquisition region of a predetermined size in the image captured by the imager as collation data, the collation data acquisition region determined based on a position defined by an external shape of the object and a position of printing information that has been printed on the object;
calculate correlation values between concentration values of respective pixels in a registration data acquisition region of a predetermined size, that are registered in advance as registration data, and concentration values of respective pixels in a corresponding region in the collation data acquisition region, the corresponding region corresponding to the registration data acquisition region determined based on an external shape of the genuine object and a position of a print pattern printed on the genuine object; and
determine that the object to be discriminated is same as the genuine object when the correlation value satisfies a predetermined criterion.

3. The genuineness determining apparatus according to claim 2, wherein:
the CPU is further configured to:
acquire feature data as collation data, the feature data representing a feature that is distributed in a region of a size including a region for acquiring registration data on the object and being larger than the region; and
sequentially select data having a same size as the registration data from the collation data, sequentially calculates a correlation value between the selected data and the registration data to consequently obtain a plurality of correlation values, and determines that the object to be discriminated is same as the object from which the registration data was acquired when a maximum of the acquired correlation values is equal to or larger than a first predetermined value and a normalized score of the maximum of the correlation values obtained by subtracting an average of the correlation values from the maximum of the correlation values and dividing a value obtained by the subtracting by a standard deviation of the correlation values is equal to or larger than a second predetermined value.

4. The genuineness discriminating apparatus according to claim 2, wherein: CPU is further configured to calculate the correlation values by a normalized correlation method to acquire the correlation values.

5. The genuineness discriminating apparatus according to claim 3, wherein: the CPU is further configured to calculate the correlation values by a normalized correlation method to acquire the correlation values.

6. The genuineness discriminating apparatus according to claim 2, wherein: the object is a tablet.

7. The genuineness discriminating apparatus according to claim 3, wherein: the object is a tablet.

8. The genuineness discriminating apparatus according to claim 4, wherein: the object is a tablet.

9. The genuineness discriminating apparatus according to claim 5, wherein: the object is a tablet.

* * * * *